United States Patent [19]
Merki et al.

[11] Patent Number: 5,002,055
[45] Date of Patent: Mar. 26, 1991

[54] APPARATUS FOR THE BIOFEEDBACK CONTROL OF BODY FUNCTIONS

[75] Inventors: Hans S. Merki, Bern; Rolf-Rainer C. Dries, Solothurn, both of Switzerland

[73] Assignee: Mic Medical Instruments Corporation, Solothurn, Switzerland

[21] Appl. No.: 252,198

[22] Filed: Sep. 30, 1988

Related U.S. Application Data

[63] Continuation-in-part of Ser. No. 857,634, Apr. 29, 1986, Pat. No. 4,774,956.

[30] Foreign Application Priority Data

Apr. 13, 1988 [DE] Fed. Rep. of Germany ....... 3812584

[51] Int. Cl.$^5$ .......................... A61B 5/00; A61M 5/14
[52] U.S. Cl. .................................... 128/635; 128/670; 128/672; 128/736; 128/DIG. 12; 604/31; 604/66; 604/67
[58] Field of Search ....... 128/635, DIG. 12, DIG. 13, 128/672, 670, 736; 604/31, 65–67; 364/413.03, 413.04, 413.09, 413.11

[56] References Cited

U.S. PATENT DOCUMENTS

| | | | |
|---|---|---|---|
| 4,080,966 | 3/1978 | McNally et al. | 604/66 X |
| 4,121,574 | 10/1978 | Lester | 128/736 X |
| 4,378,014 | 3/1983 | Elkow | 604/31 |
| 4,381,011 | 4/1983 | Somers, 3rd | 128/635 |
| 4,551,133 | 11/1985 | Beyl | 128/DIG. 12 |
| 4,633,878 | 1/1987 | Bombardieri | 604/31 X |
| 4,676,776 | 6/1987 | Howson | 604/31 |
| 4,718,891 | 1/1988 | Lipps | 604/31 |
| 4,774,956 | 10/1988 | Kruse et al. | 128/635 |
| 4,878,896 | 11/1989 | Garrison et al. | 128/DIG. 12 X |

FOREIGN PATENT DOCUMENTS

| | | | |
|---|---|---|---|
| 3018641 | 6/1981 | Fed. Rep. of Germany | 604/31 |
| 8101794 | 7/1981 | World Int. Prop. O. | 604/31 |
| 8500292 | 1/1985 | World Int. Prop. O. | 604/31 |

*Primary Examiner*—Lee S. Cohen
*Attorney, Agent, or Firm*—Kenyon & Kenyon

[57] ABSTRACT

An apparatus for the biofeedback control of body functions is proposed having at least one sensor for detecting biological body functions, a data memory for storing comparison values, a control unit or microprocessor (9, 16) and a therapy member, the control means (9, 16) activating the therapy system as a function of the measured values detected by the sensor and the comparison values. The therapy systems has a pump for the intravenous, intra-arterial, oral or intraluminal administration and a drug reservoir connected to the pump. The control unit and/or therapy means is provided with a memory, which stores the therapy objectives for the body functions with associated drug doses as a function of the detected measured values and comparison values. The pump is activated in such a way that it delivers the drug to the desired administration point from the reservoir in accordance with the predetermined doses, the sensor continuously detecting the effects of the drugs and in accordance with the action, a change is made to the activation of the pump.

8 Claims, 49 Drawing Sheets

SH. 1/2

SH. 2/2

APPARATUS FOR THE BIOFEEDBACK CONTROL OF BODY FUNCTIONS

RELATED APPLICATIONS

This application is a continuation-in-part application to application Ser. No. 857,634 filed Apr. 29, 1986, now U.S. Pat. No. 4,774,956.

BACKGROUND OF THE INVENTION a. Field of Invention

The invention relates to an apparatus for the biofeedback control of body functions, by monitoring these functions and administering medication automatically if these functions are outside predetermined limits.

b. Description of the Prior Art

DE-OS 36 04 986 discloses an apparatus for preventing oxygen deficiency damage and for removing breathing disturbances having sensors linked with the breathing or with the oxygen supply of the tissue. If the measured values detected by these sensors are above or below predetermined threshold values, switching devices are activated, which provide breathing stimuli by a special respiratory gas mixture being blown against the patient or breathing initiating stimuli.

SUMMARY OF THE INVENTION

The present invention provides an apparatus which permits a continuous monitoring of biological body functions and the automatic administration of medication to a patient.

The apparatus includes a therapy means with at least one pump for the intravenous, intra-arterial, oral or intraluminal administration and a medication reservoir linked with the pump, in which the pump is activated as a function of the measurements of the body functions. The medication doses are administered as a function of the measured values and a preselected threshold or target point. The sensor continuously determines the effect of the medicament and selectively controls the operation of the pump. In this manner the apparatus can perform a precise, continuous and effective therapy of different body functions.

DETAILED DESCRIPTION OF THE INVENTION

Figure 1:
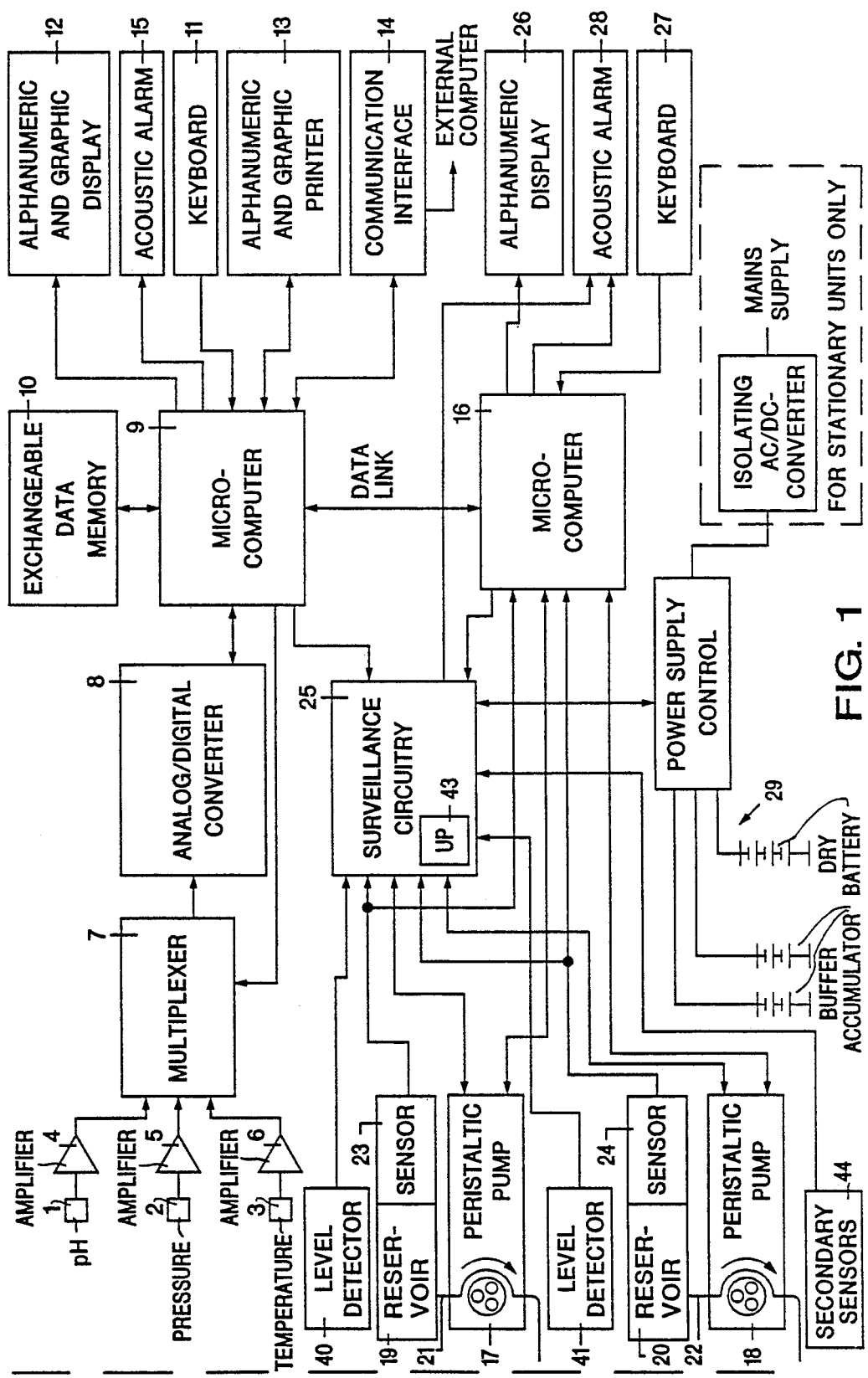
FIG. 1 shows a block diagram of an apparatus constructed in accordance with the inventions.
Figure 2A:
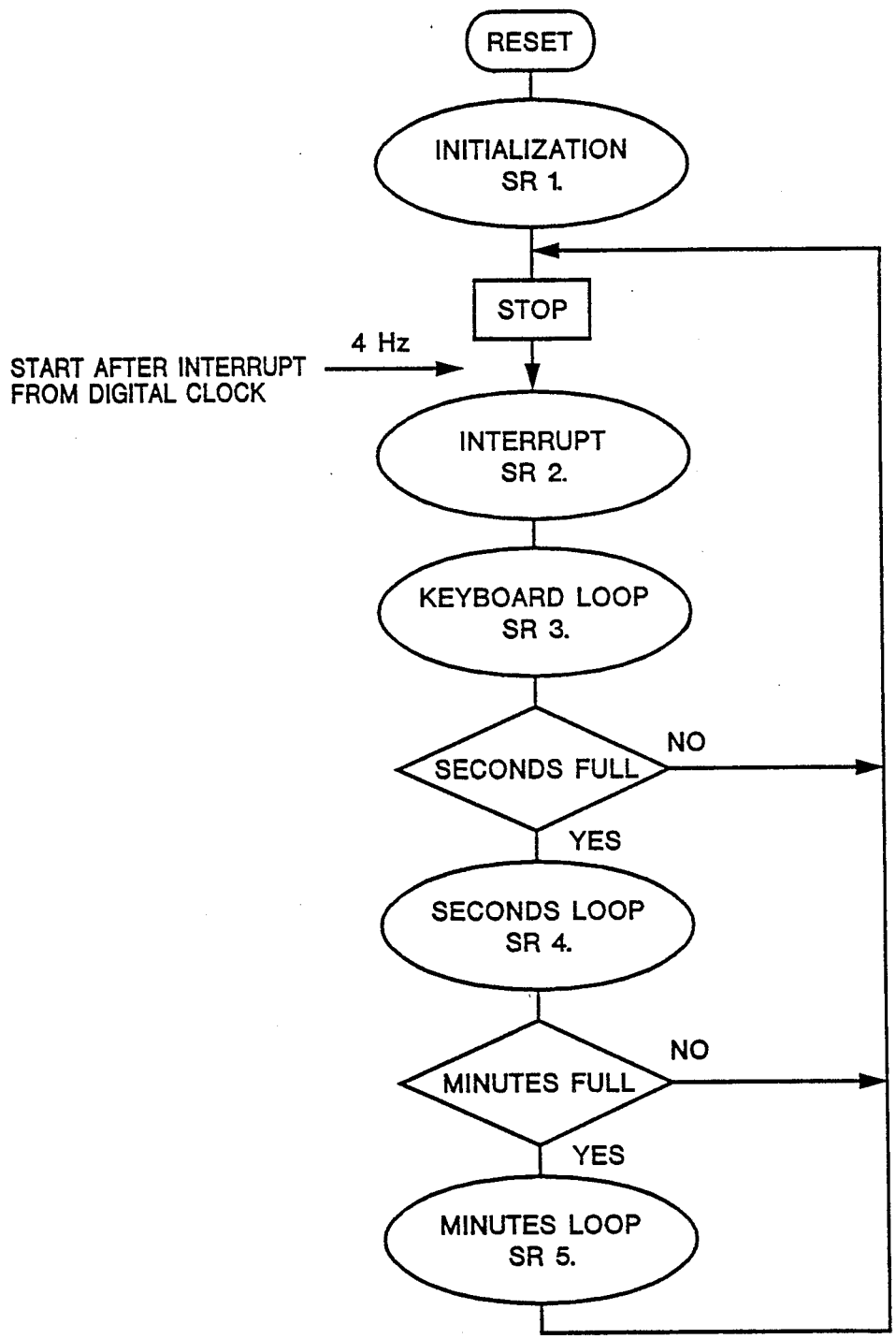
FIGS. 2A-2UU show a flow chart for the apparatus of FIG. 1.
Figure 2B:
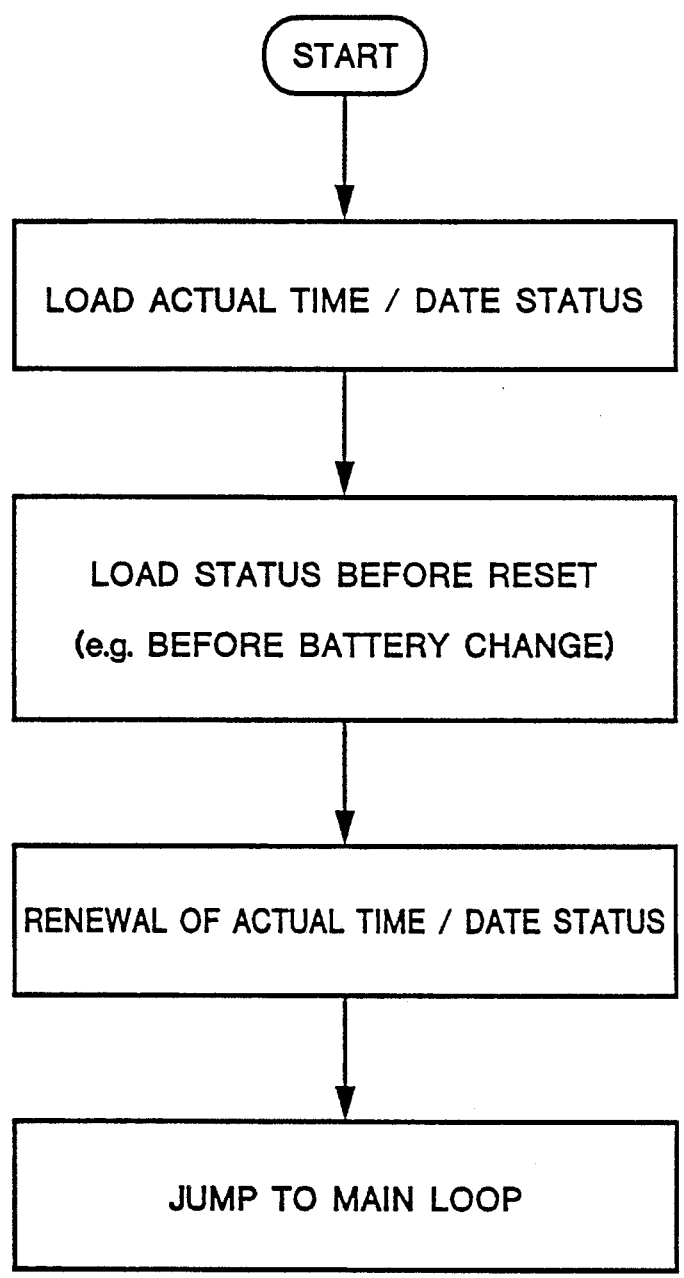
Figure 2C:
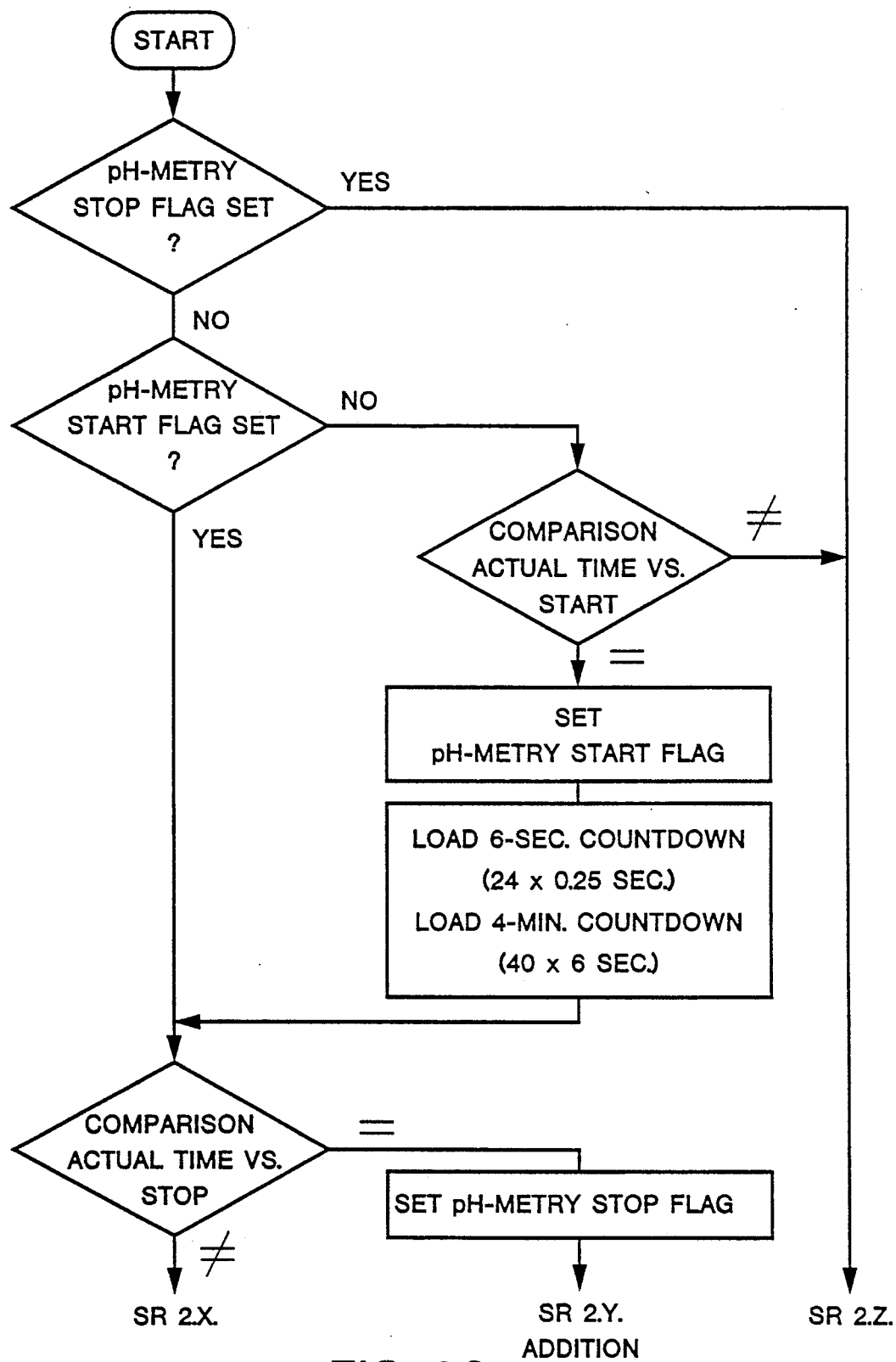
Figure 2D:
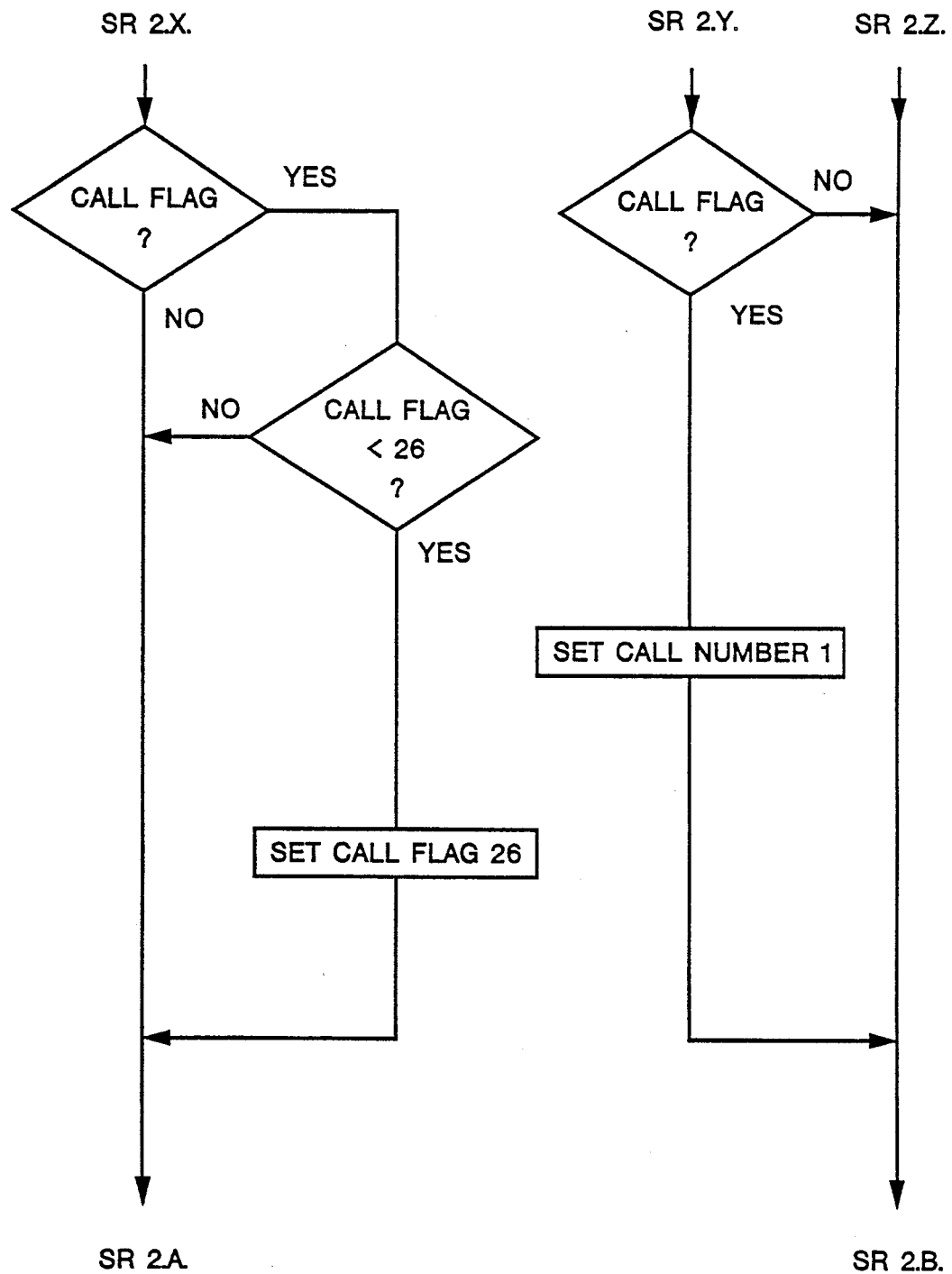
Figure 2E:
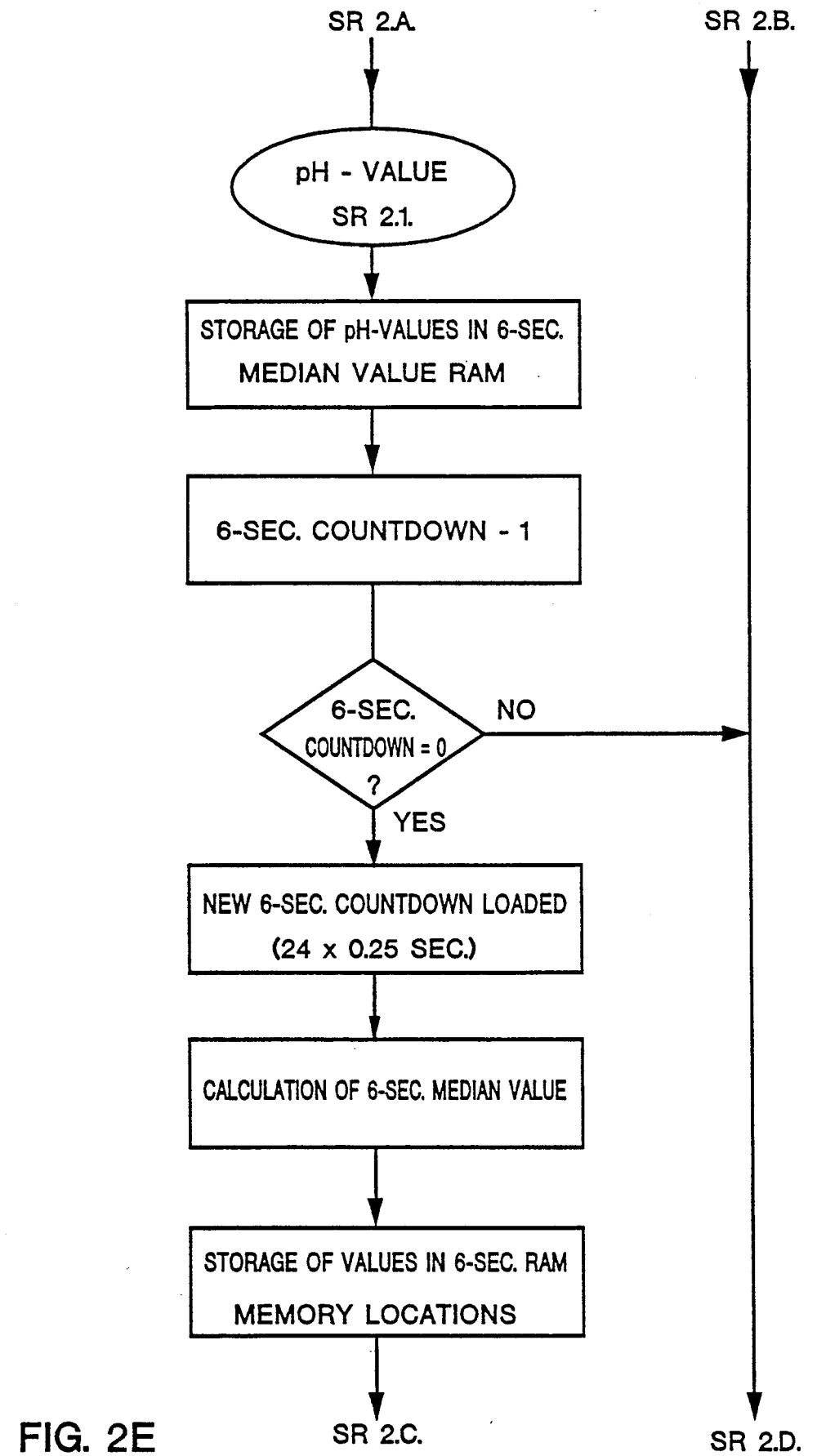
Figure 2F:
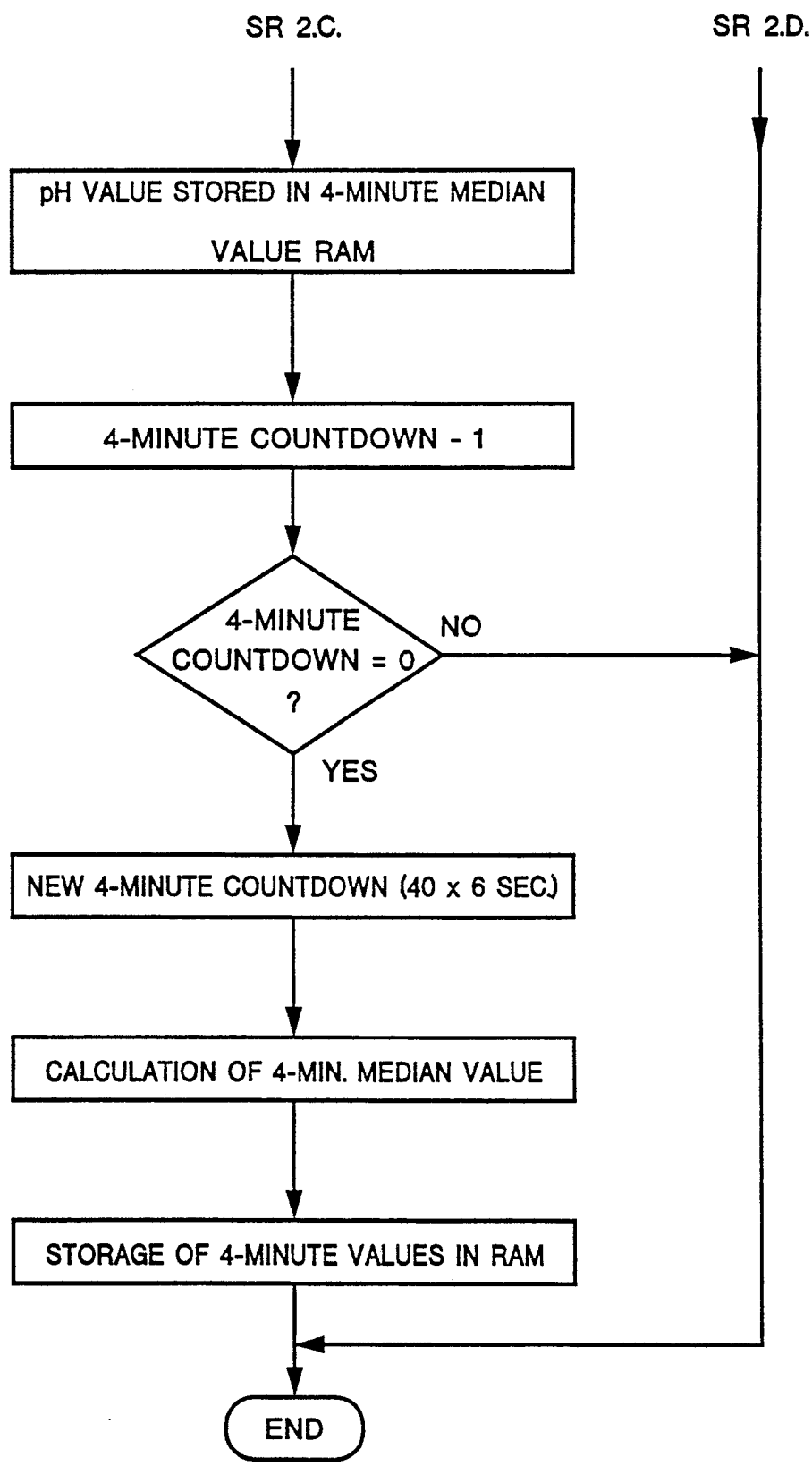
Figure 2G:
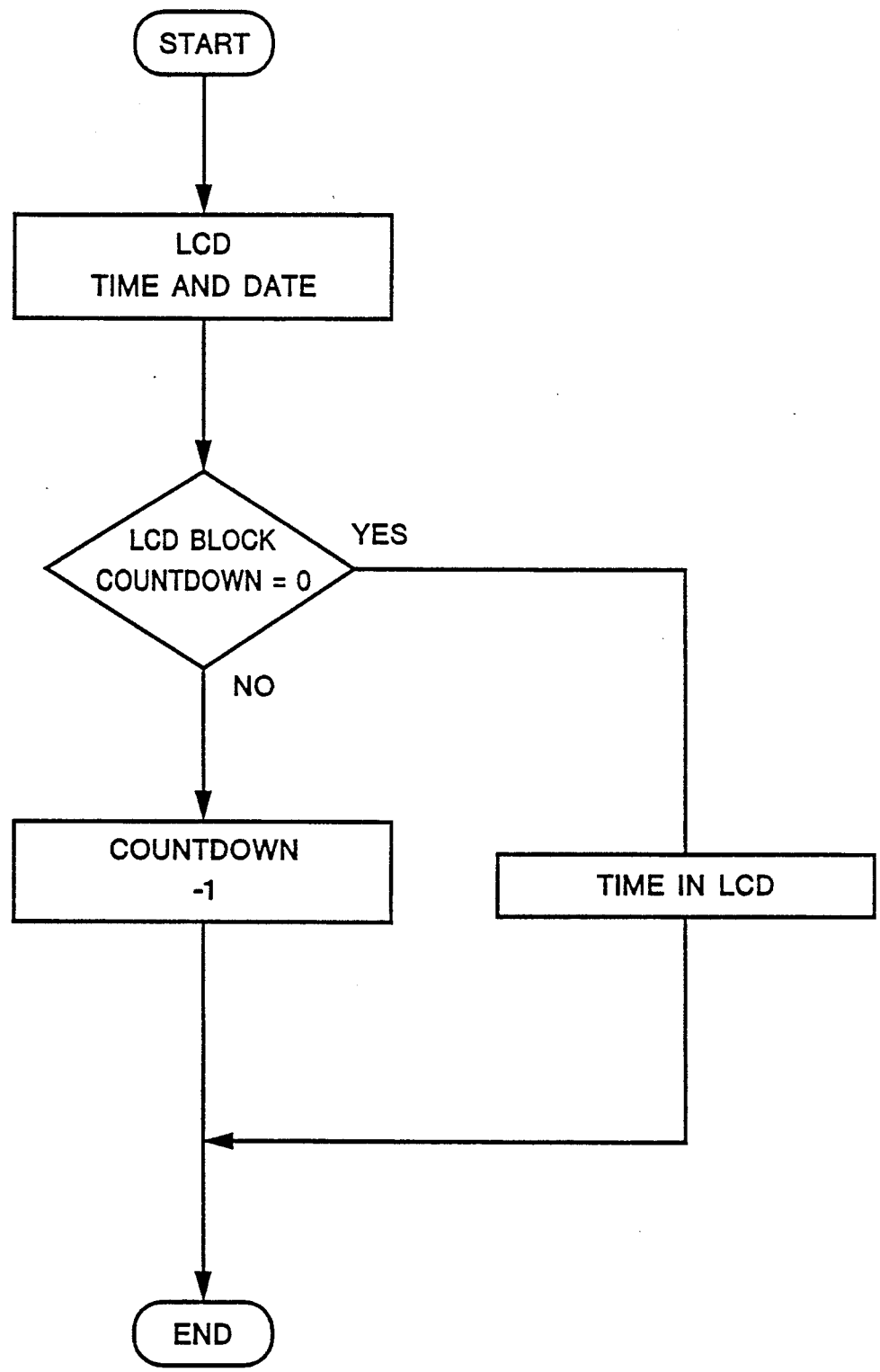
Figure 2H:
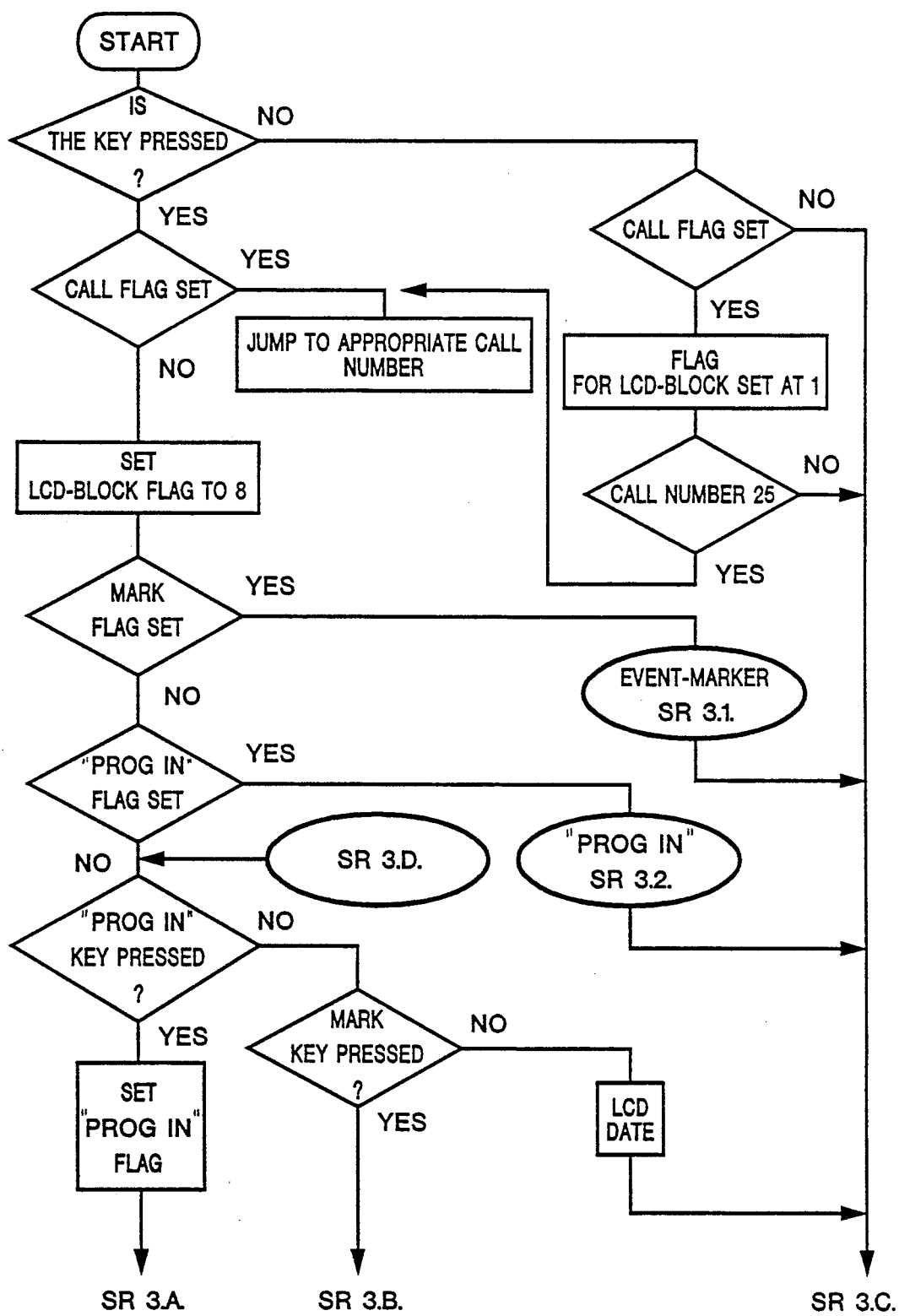
Figure 2I:
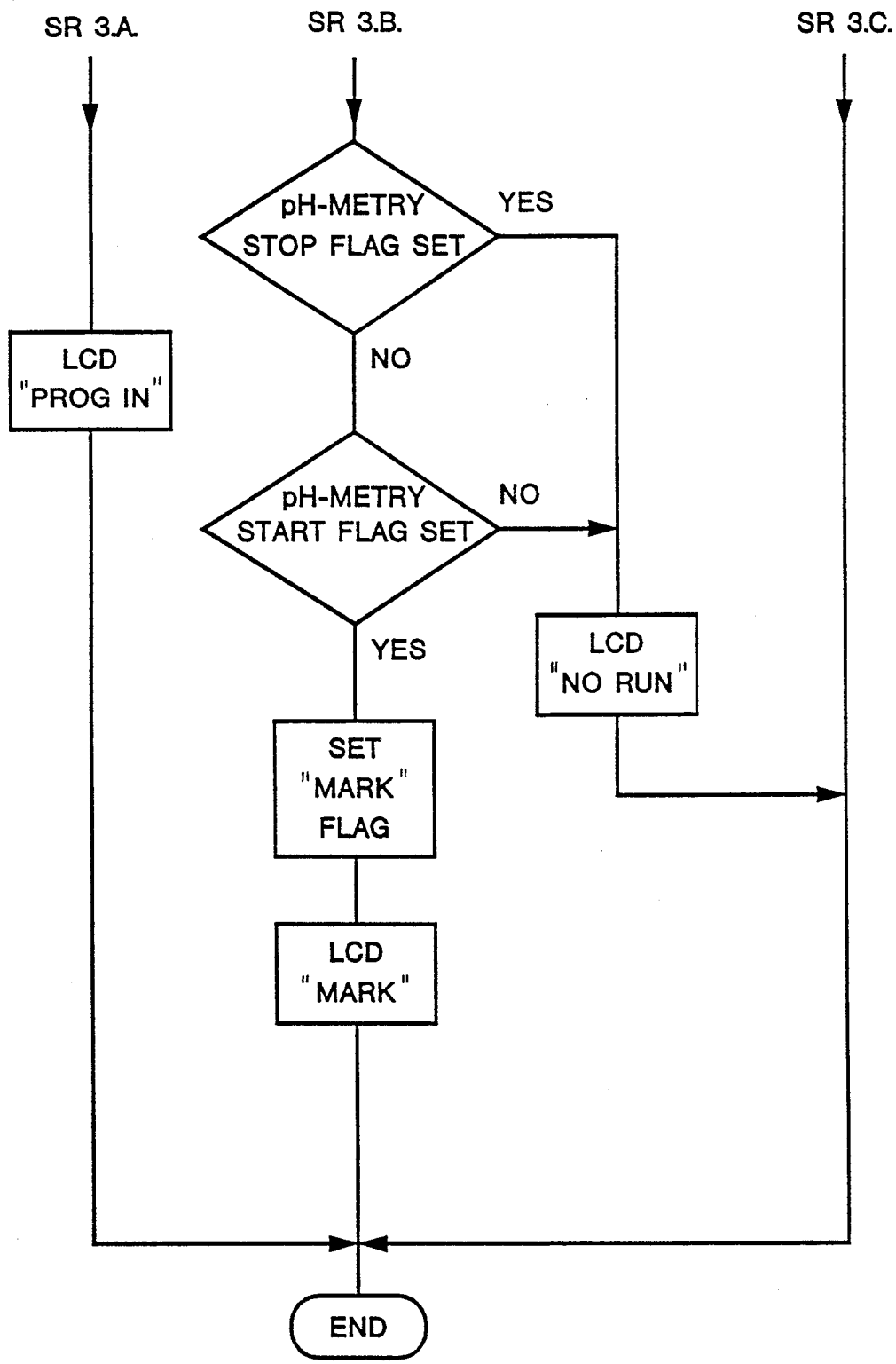
Figure 2J:
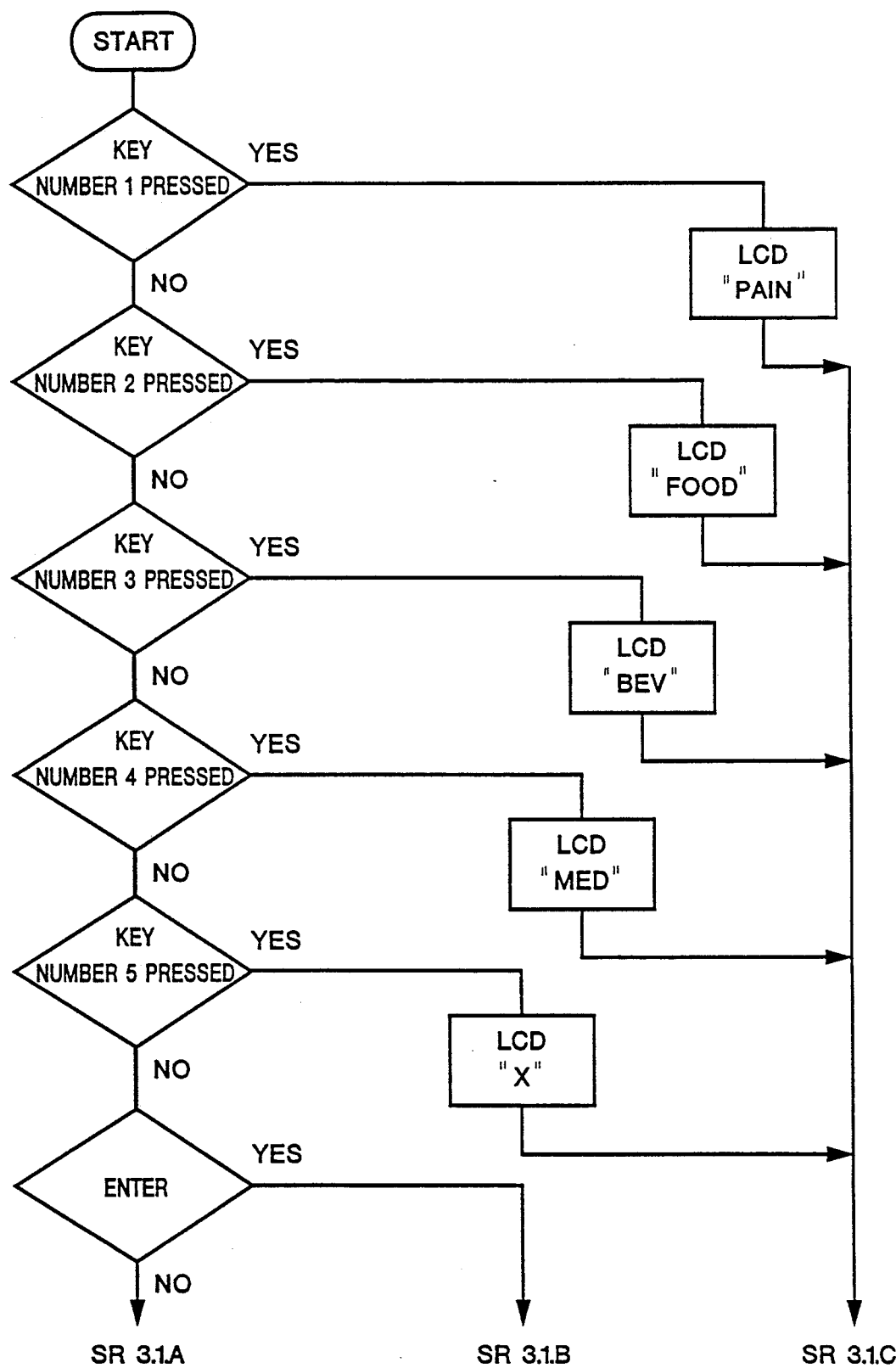
Figure 2K:
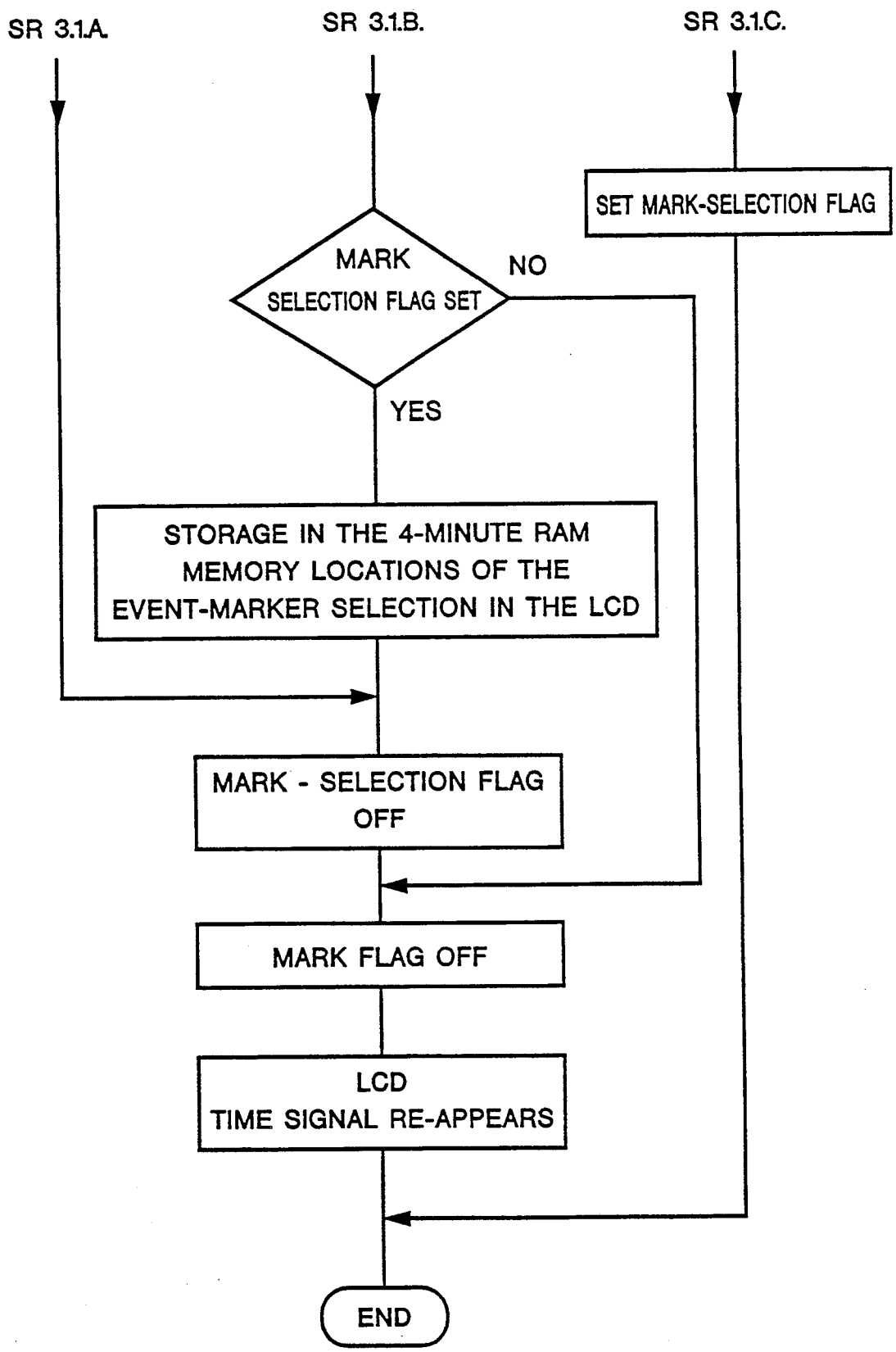
Figure 2L:
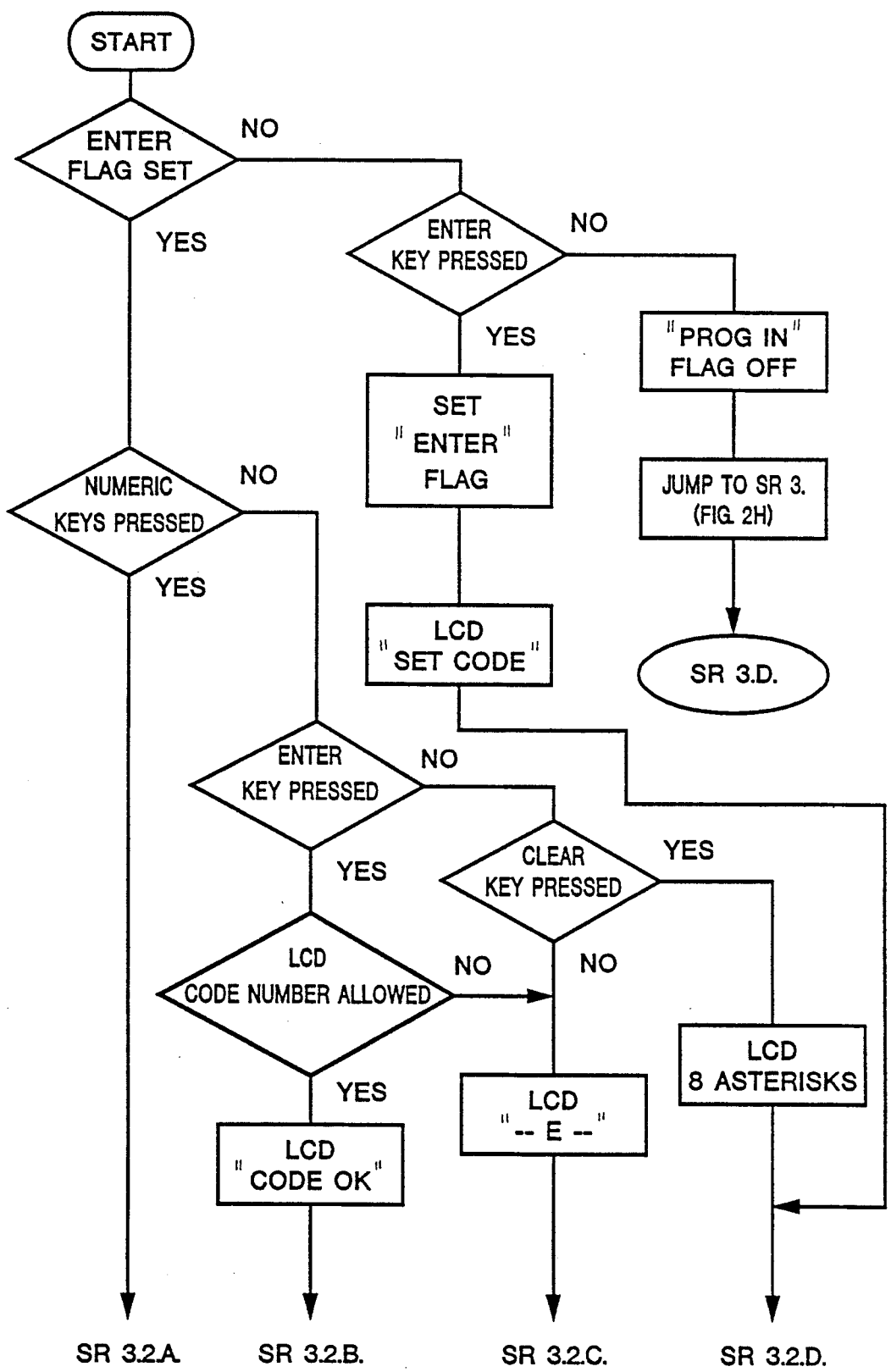
Figure 2M:
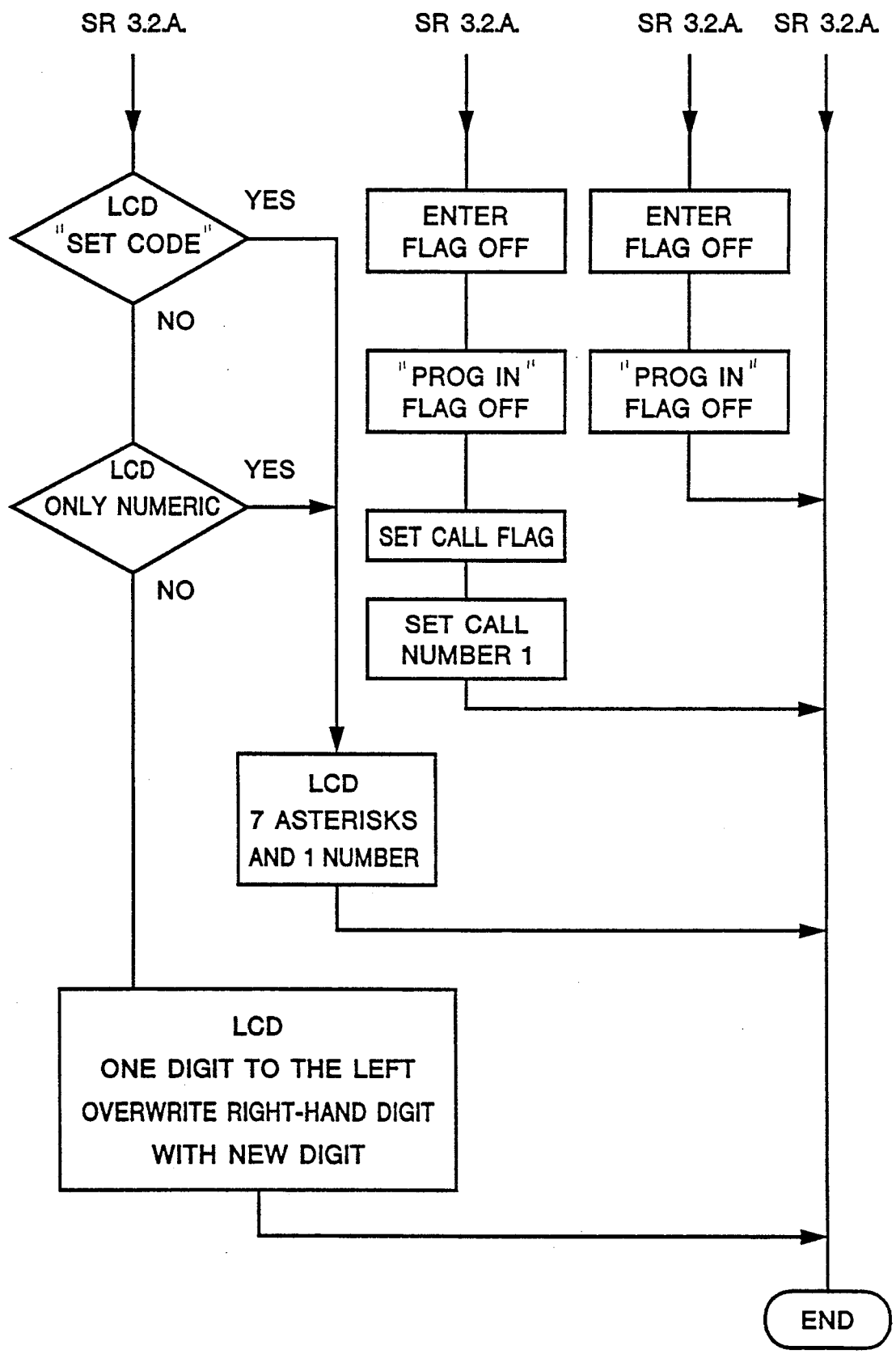
Figure 2N:
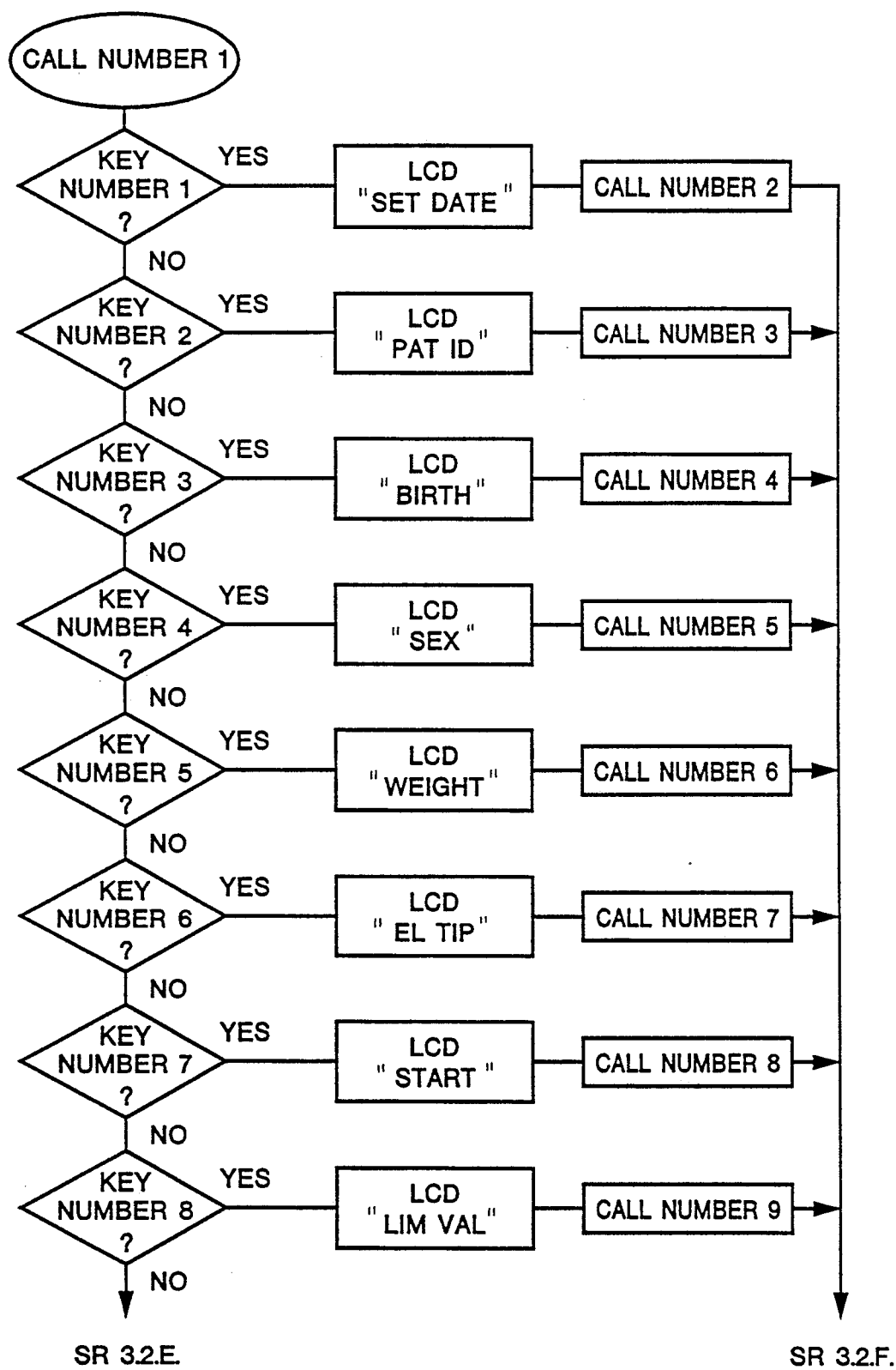
Figure 2O:
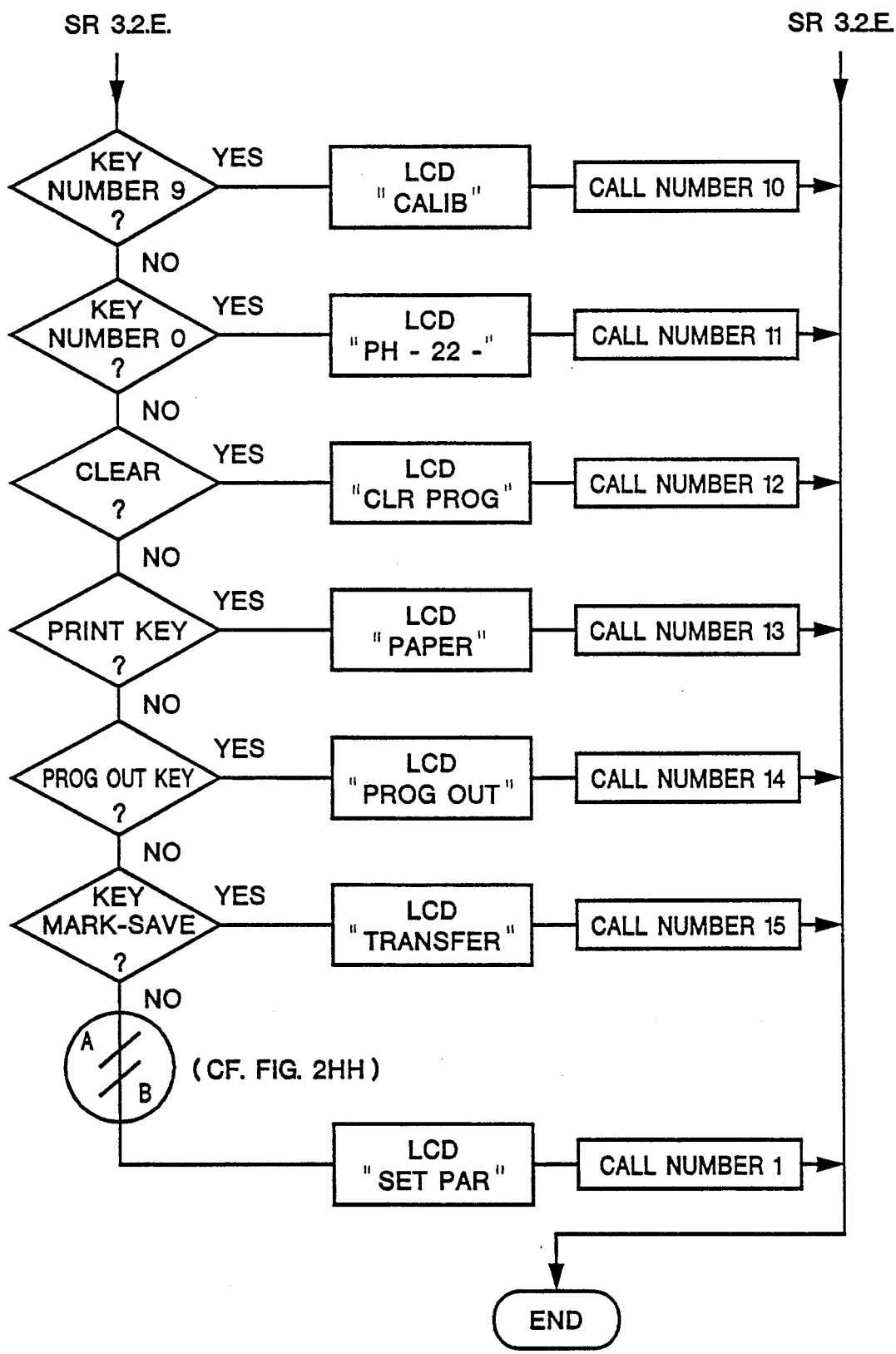
Figure 2P:
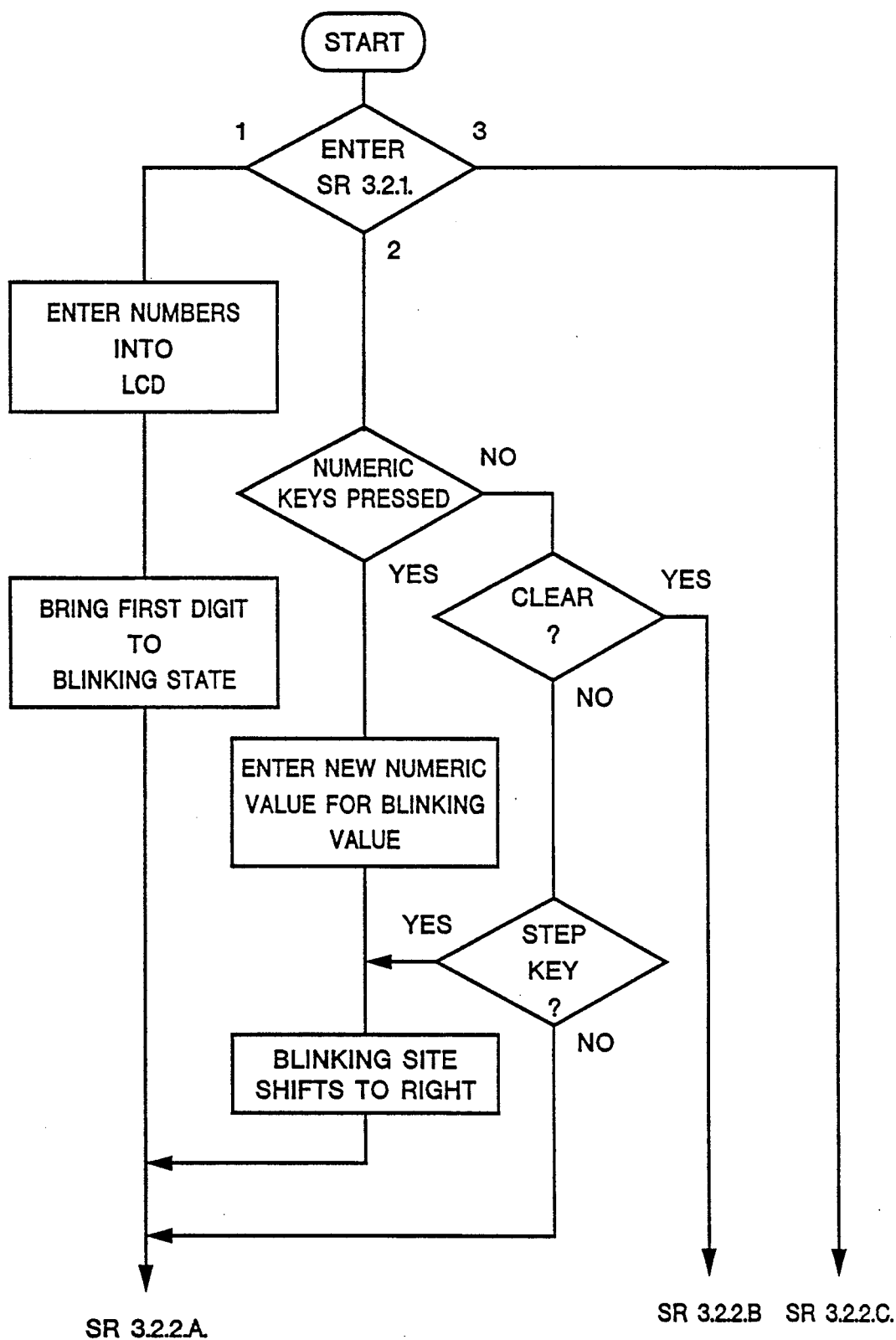
Figure 2Q:
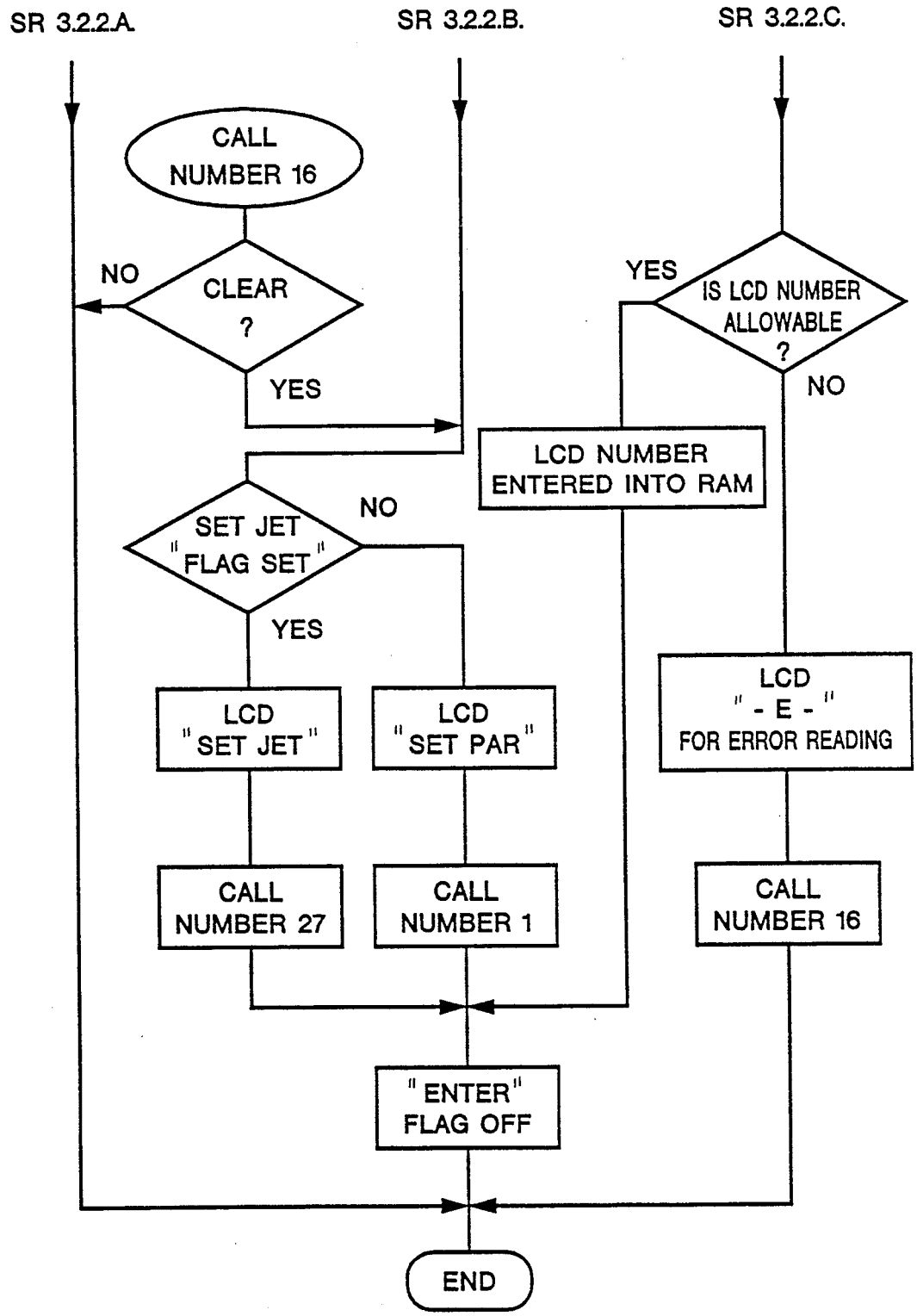
Figure 2R:
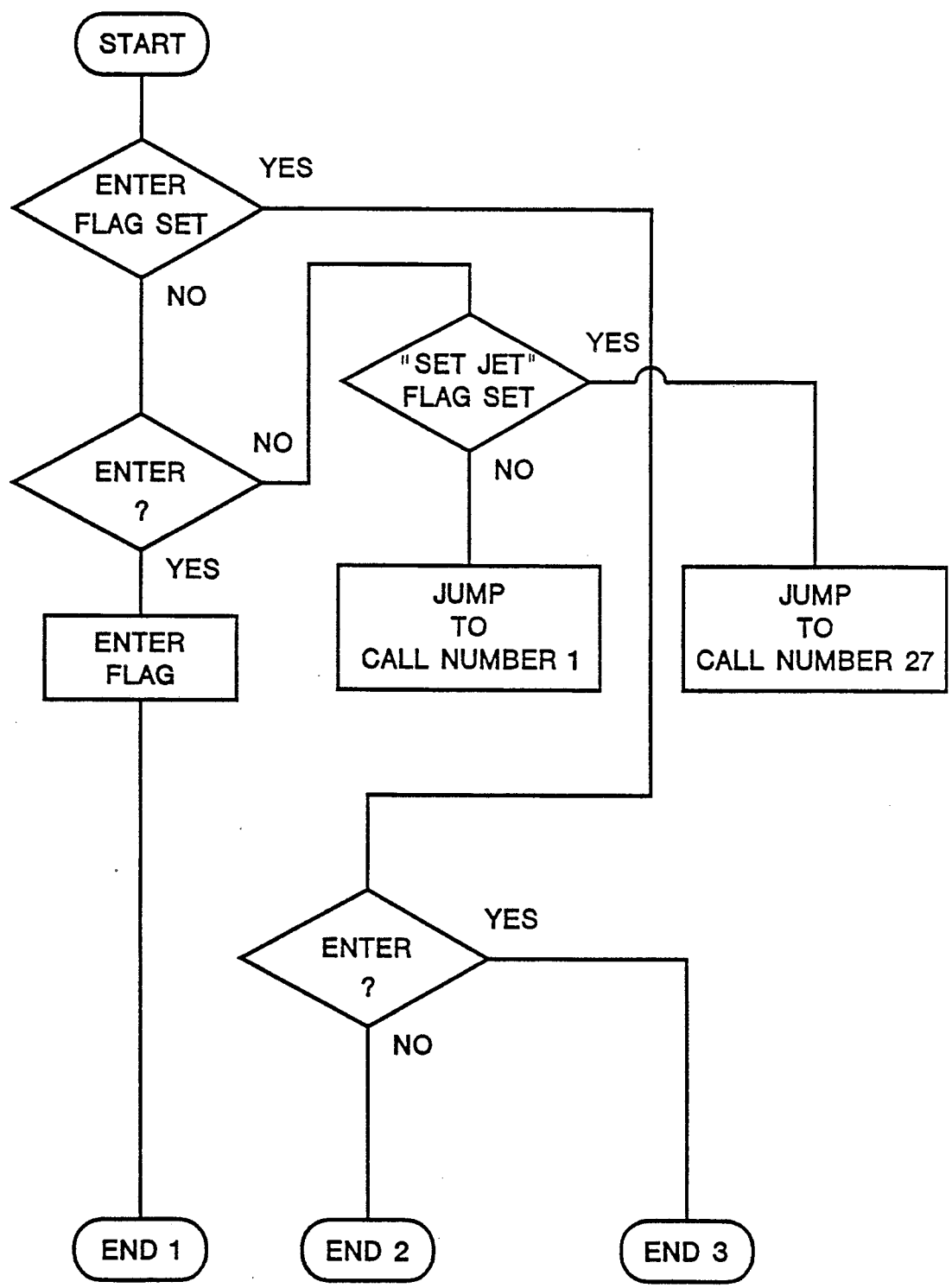
Figure 2S:
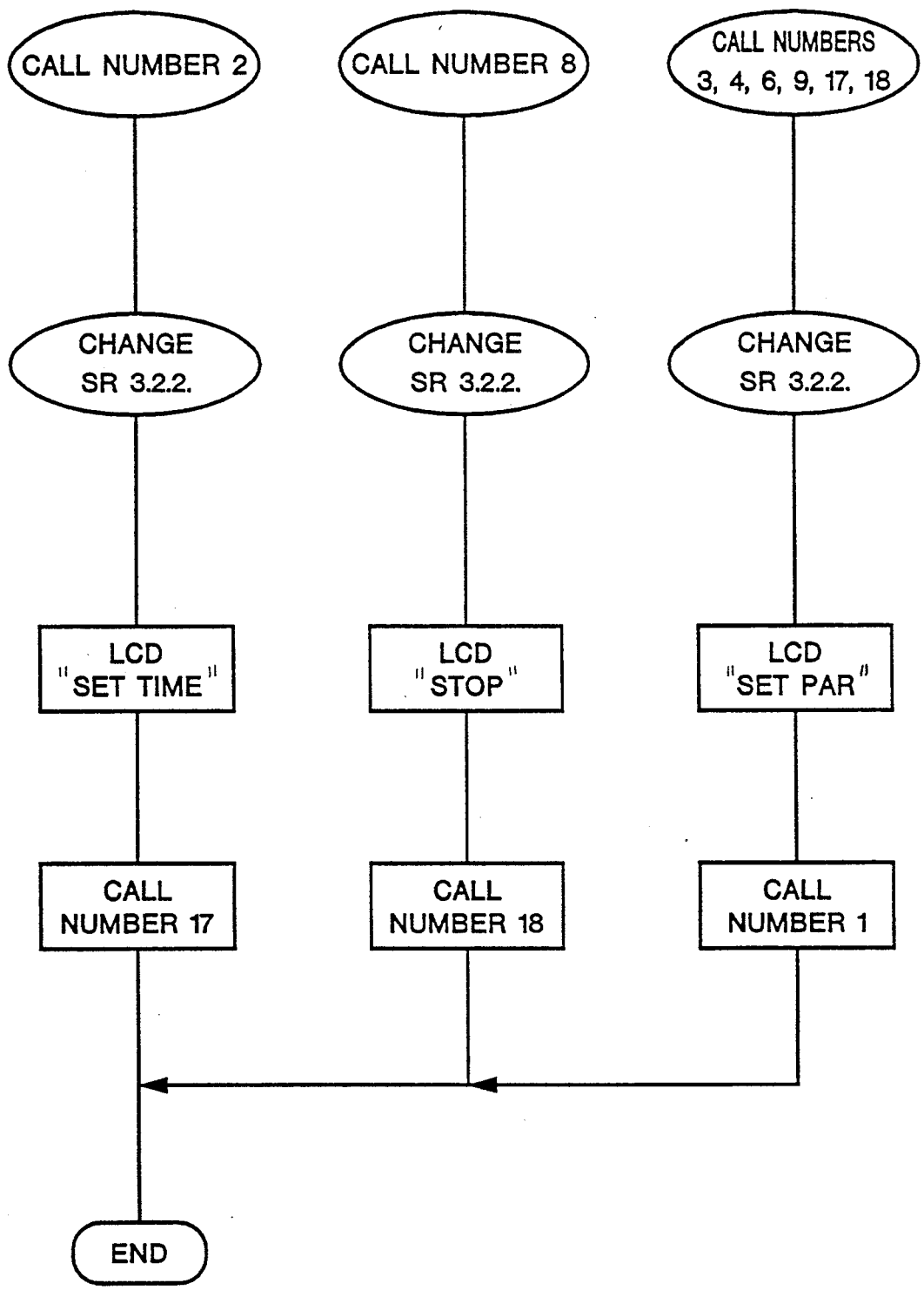
Figure 2T:
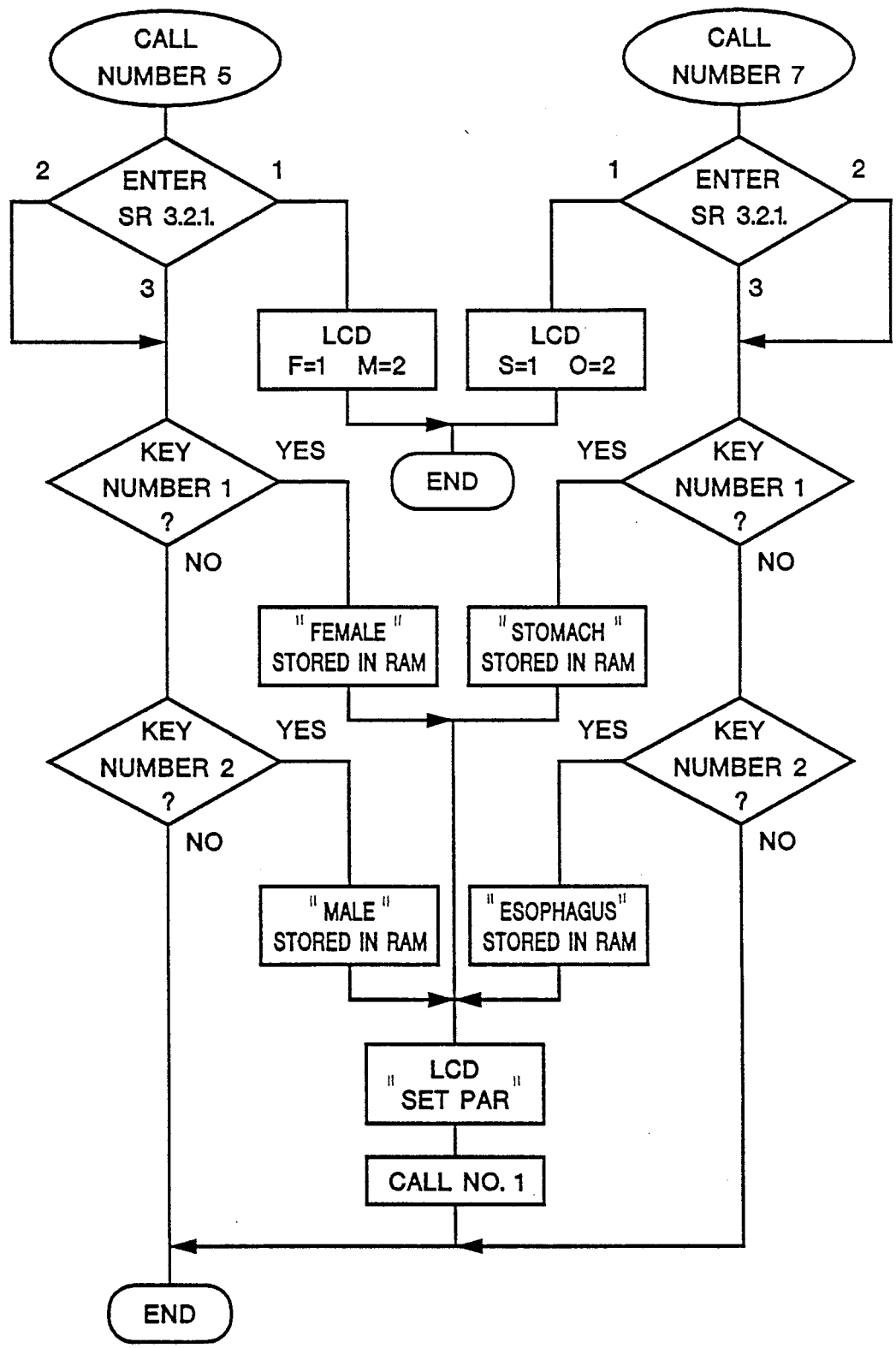
Figure 2U:
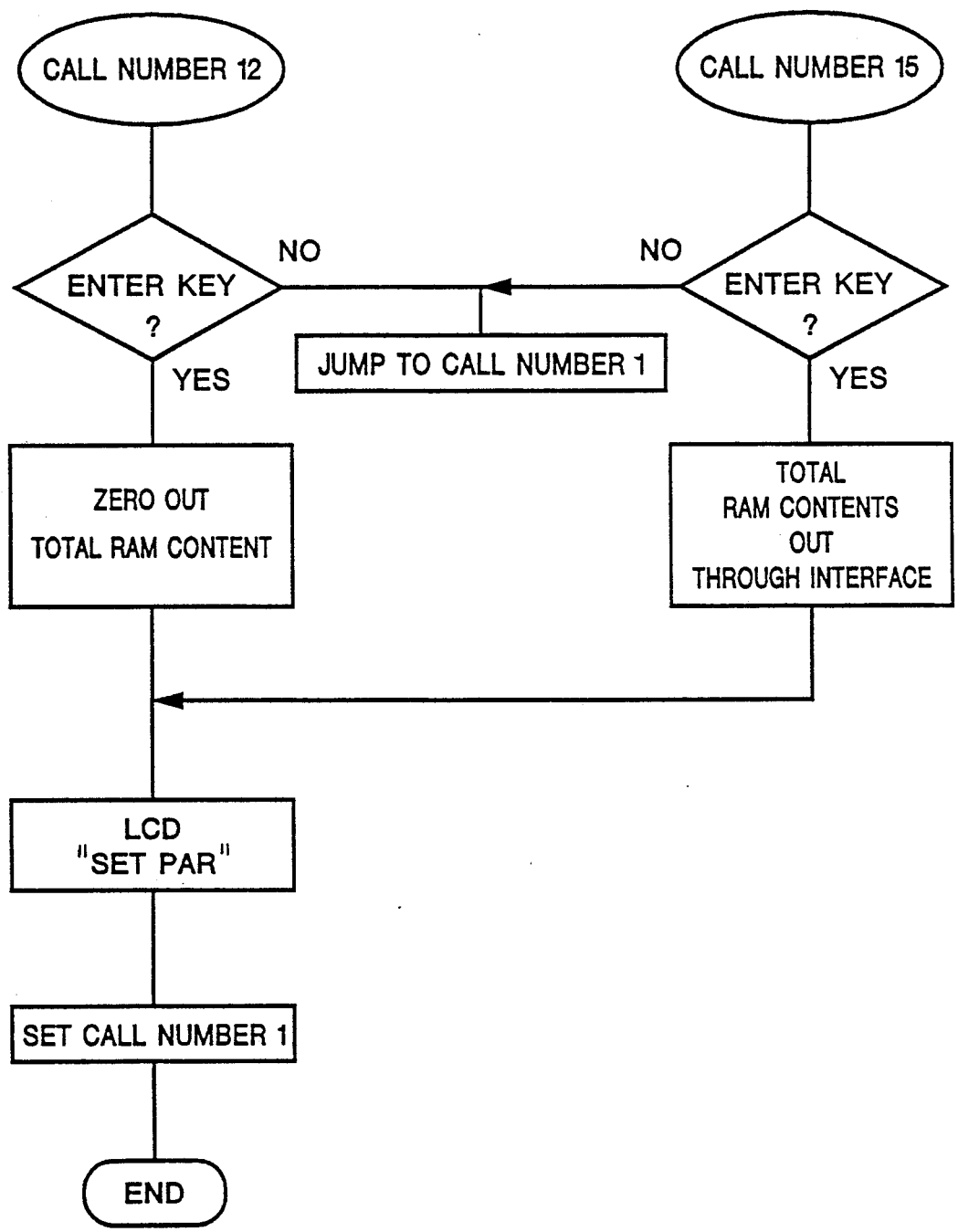
Figure 2V:
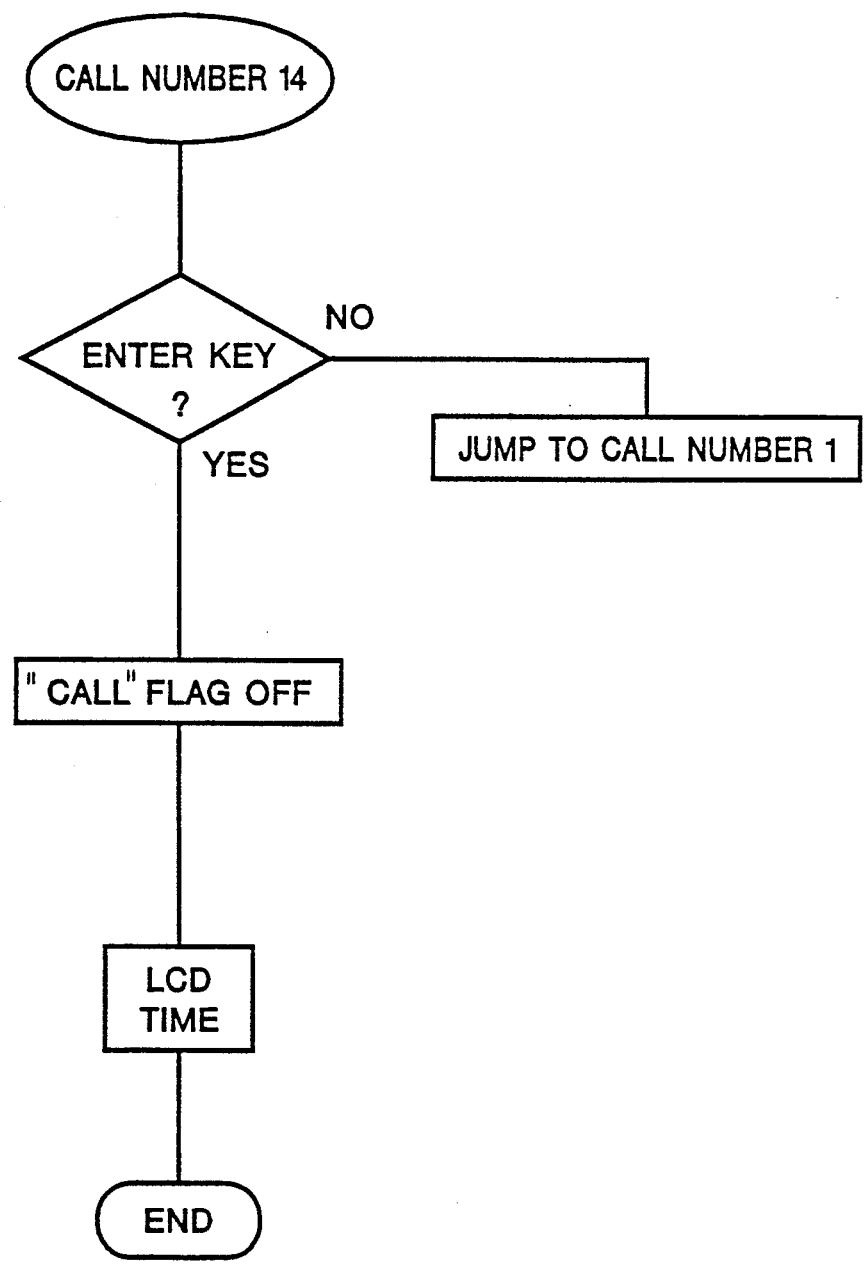
Figure 2W:
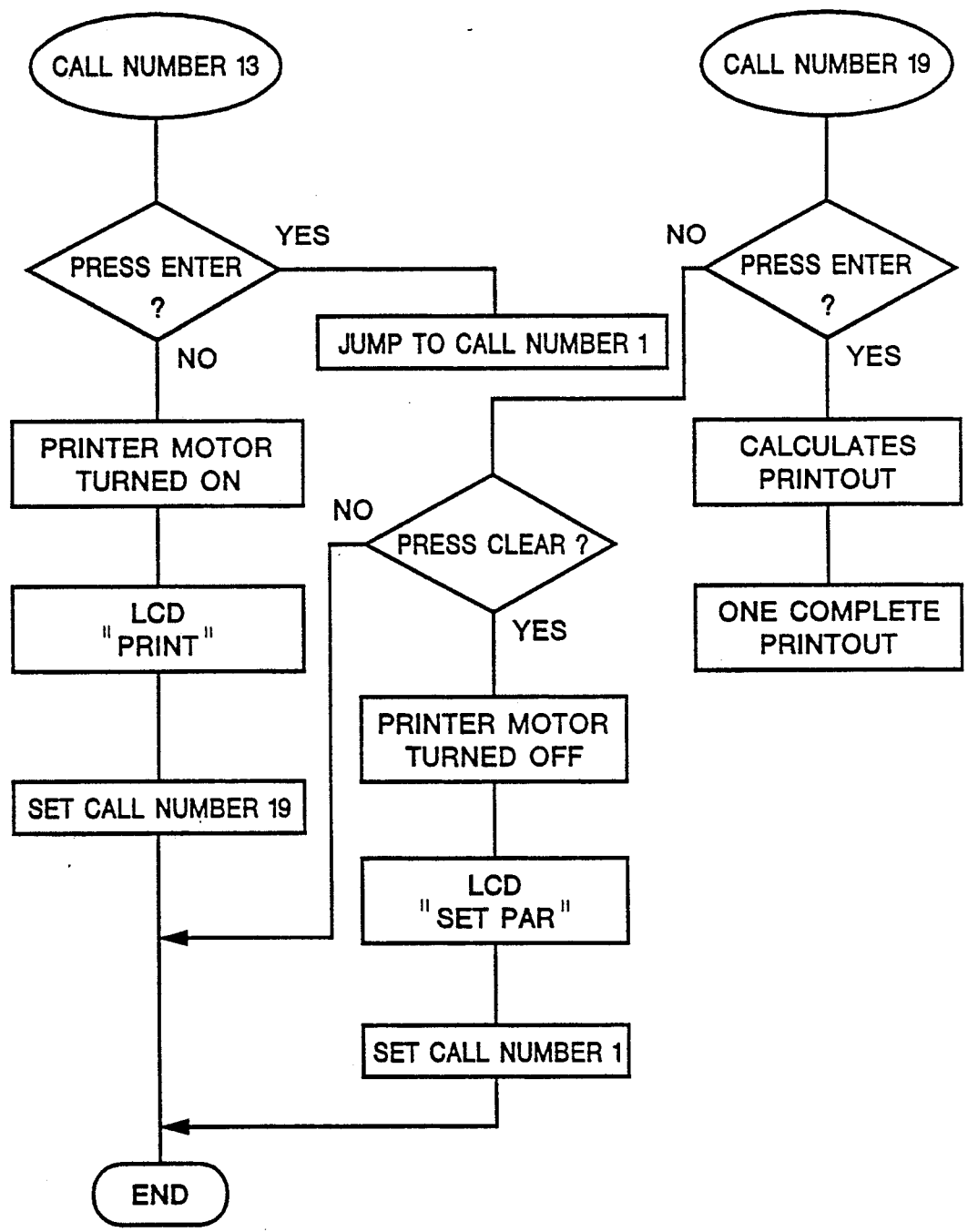
Figure 2X:
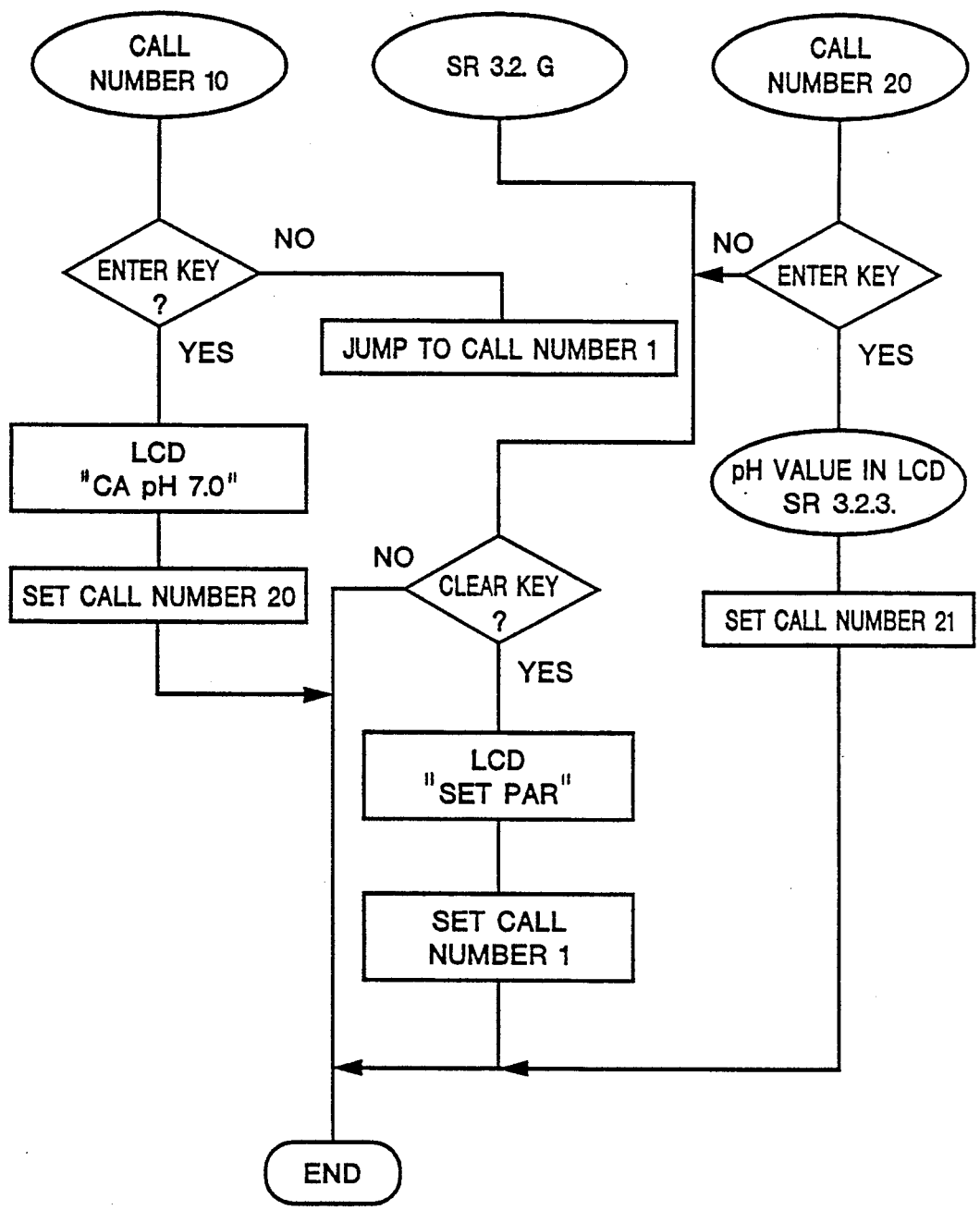
Figure 2Y:
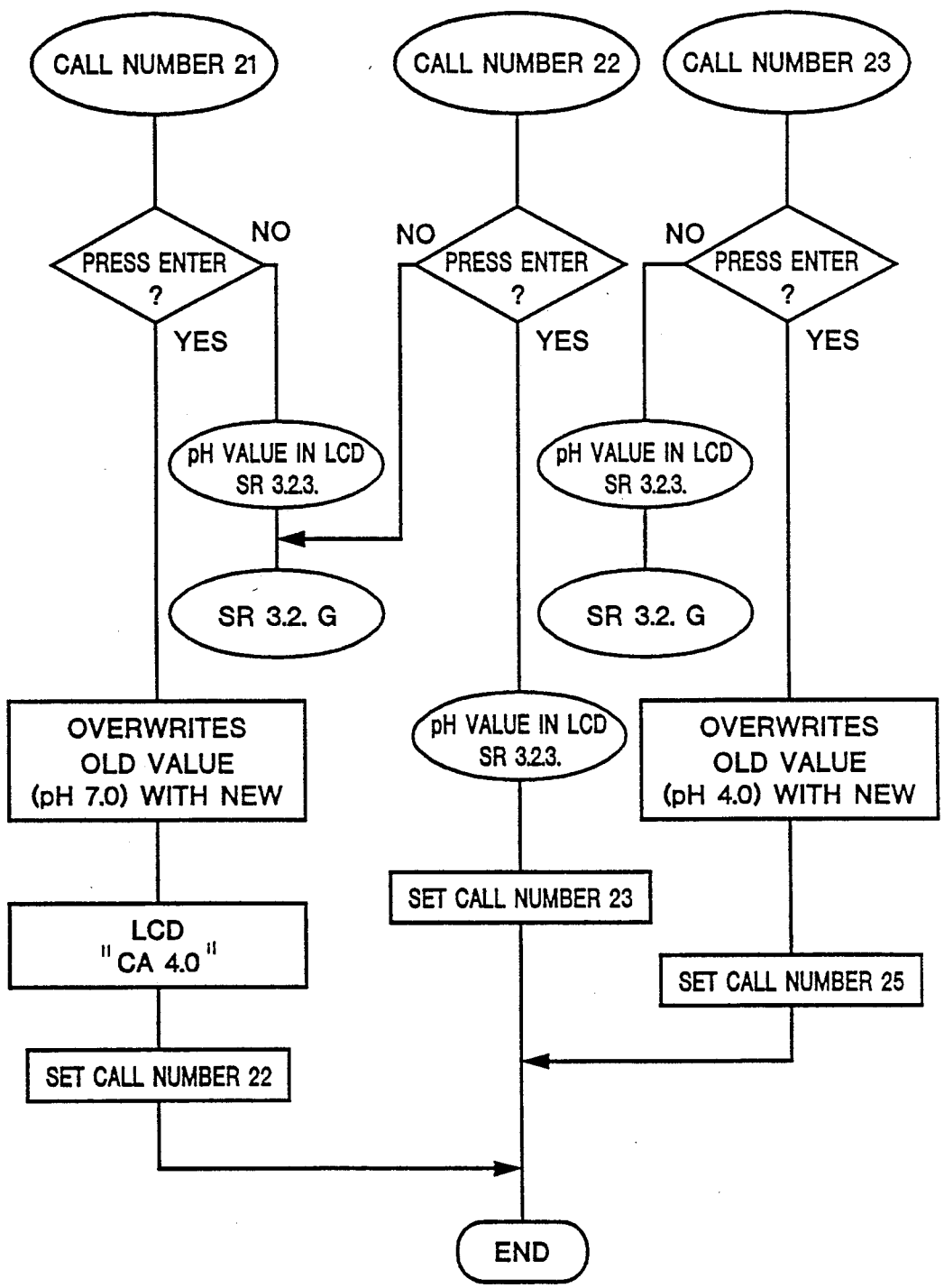
Figure 2Z:
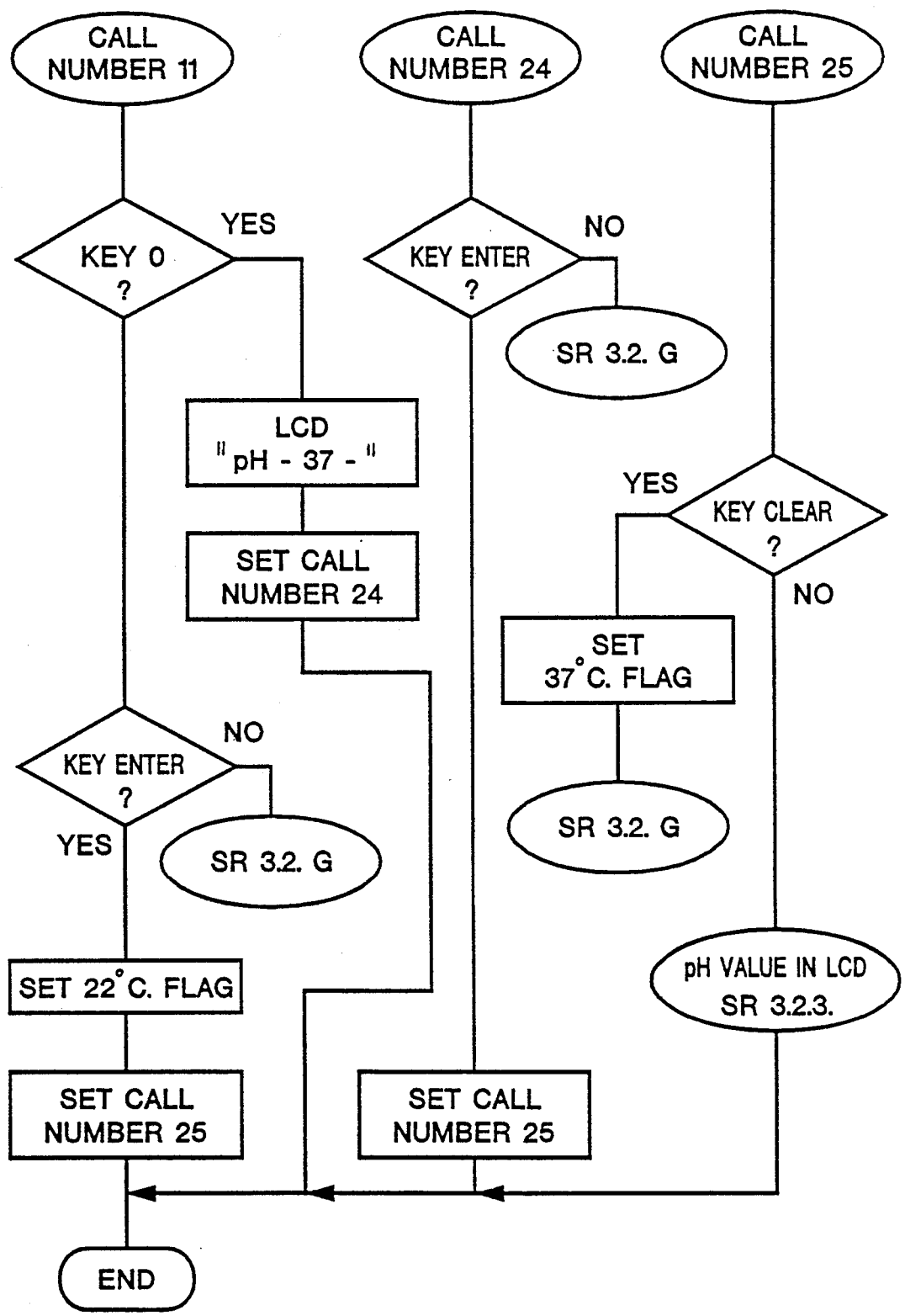
Figure 2A:
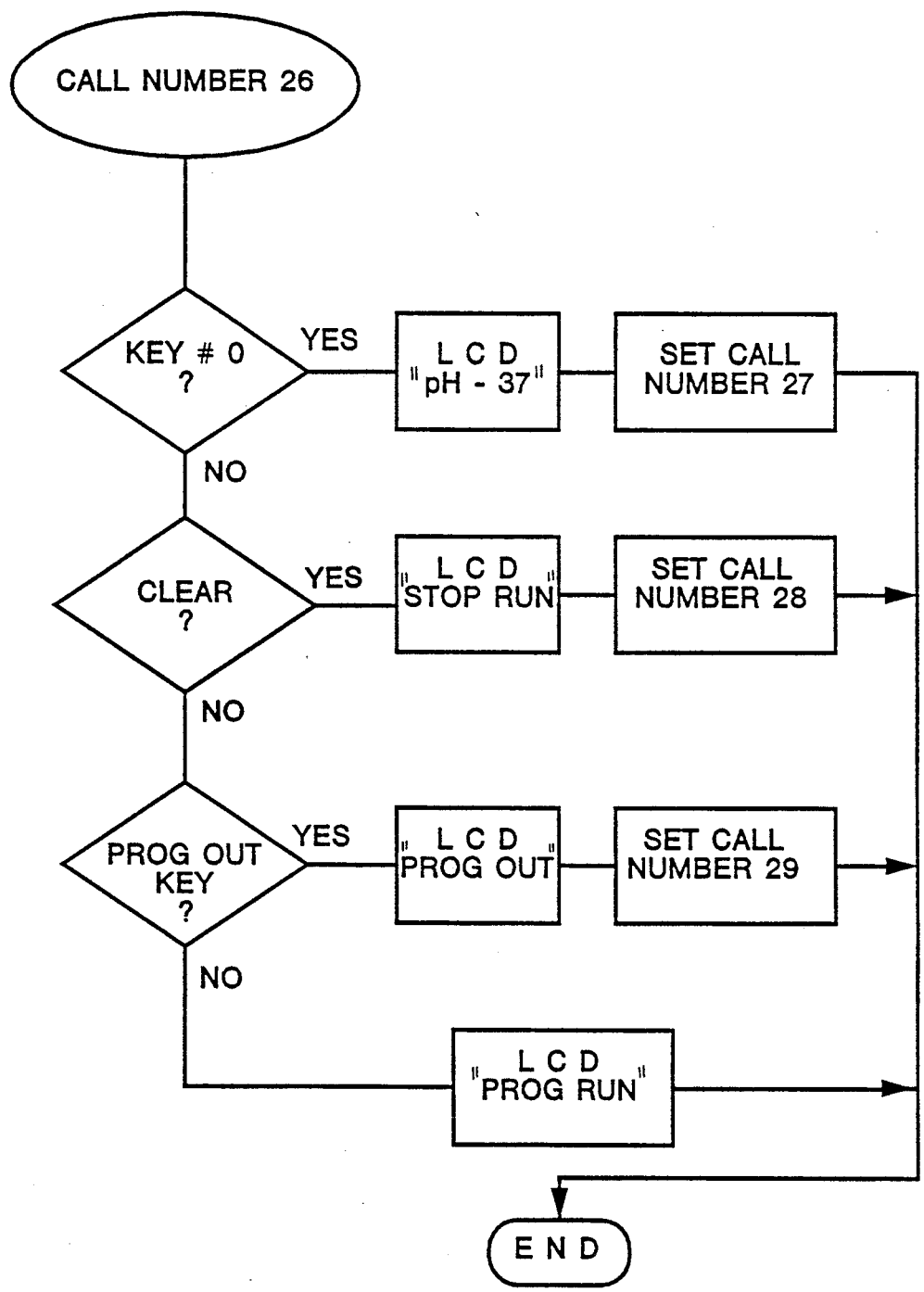
Figure 2B:
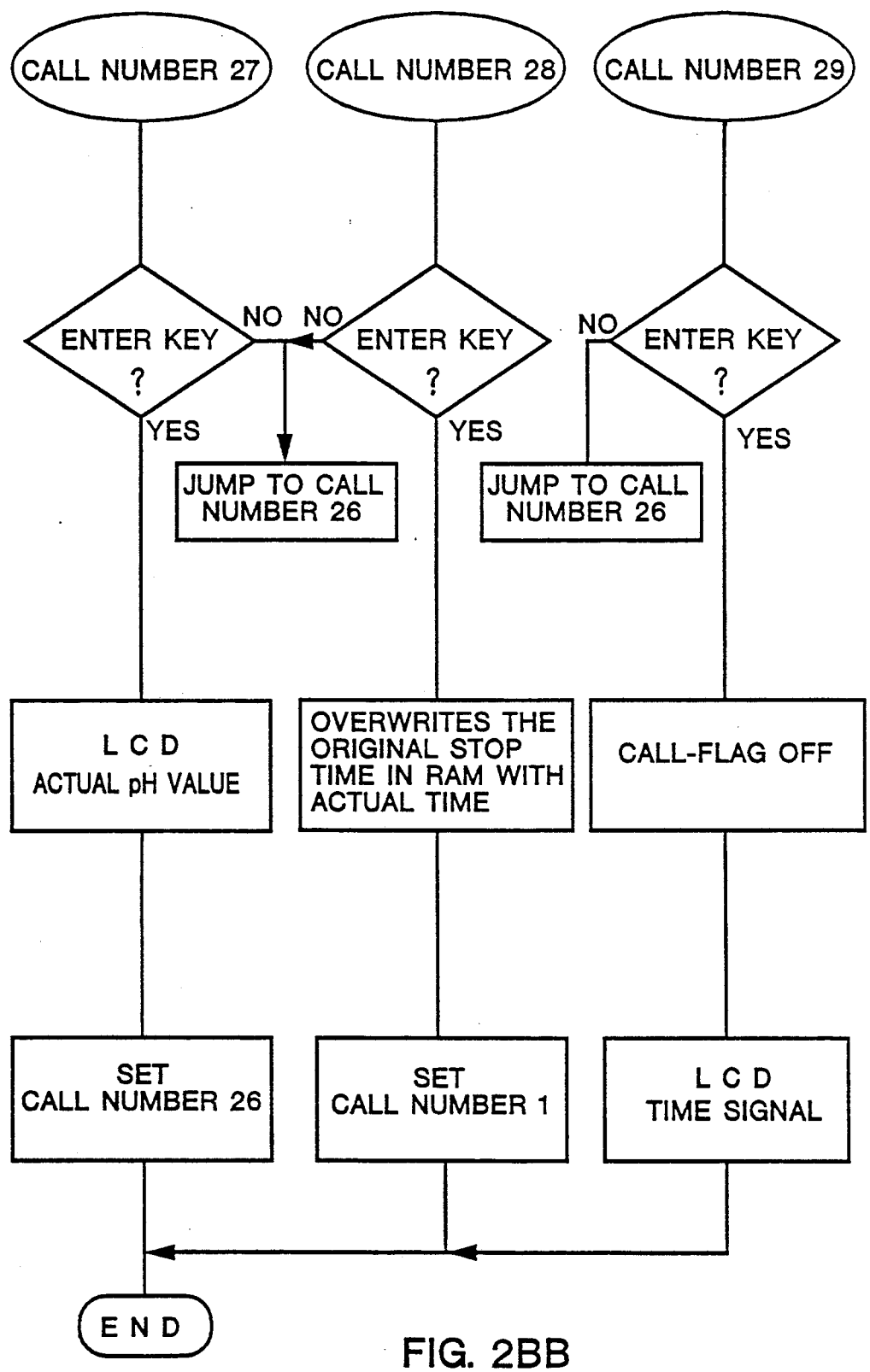
Figure 2C:
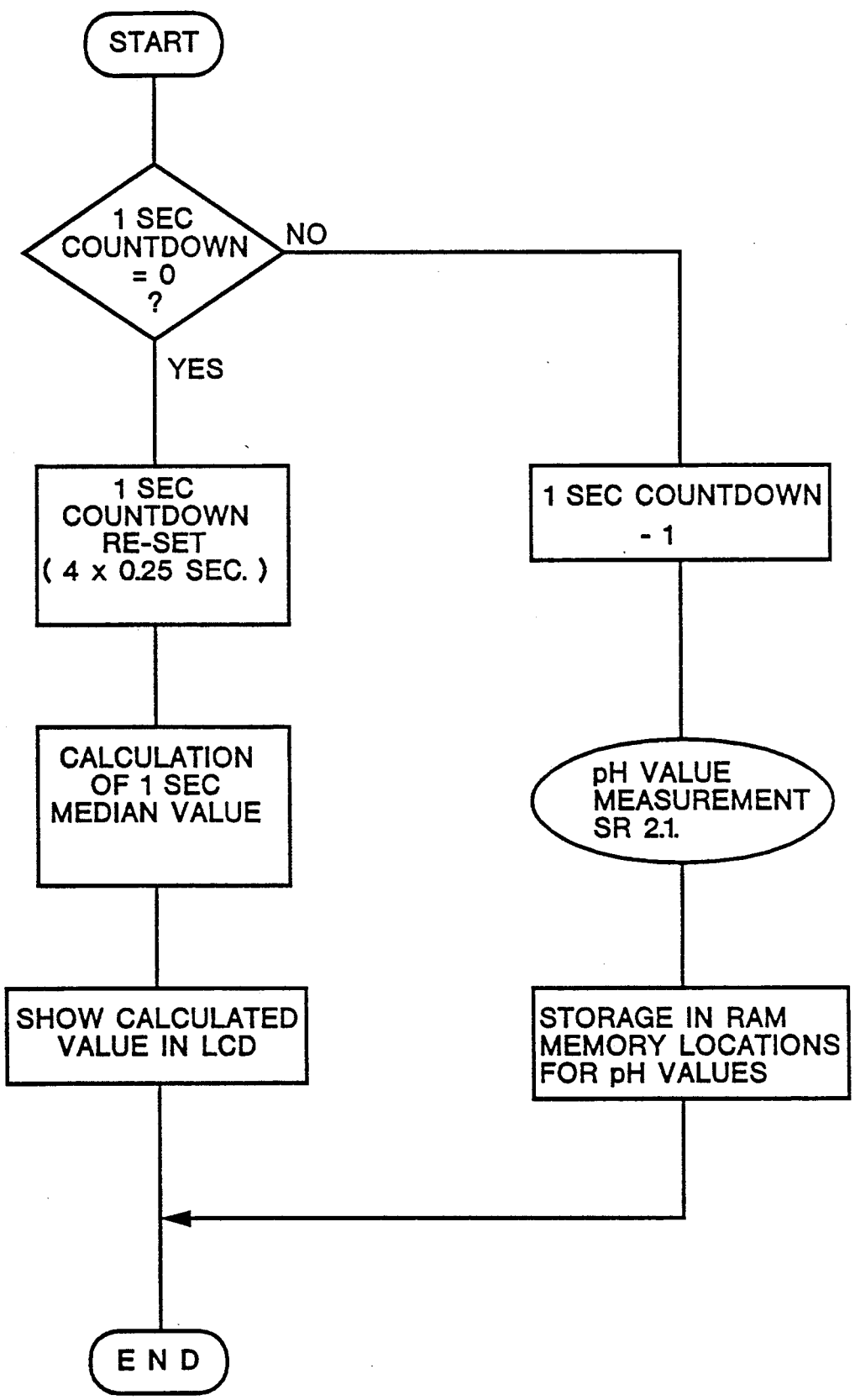
Figure 2D:
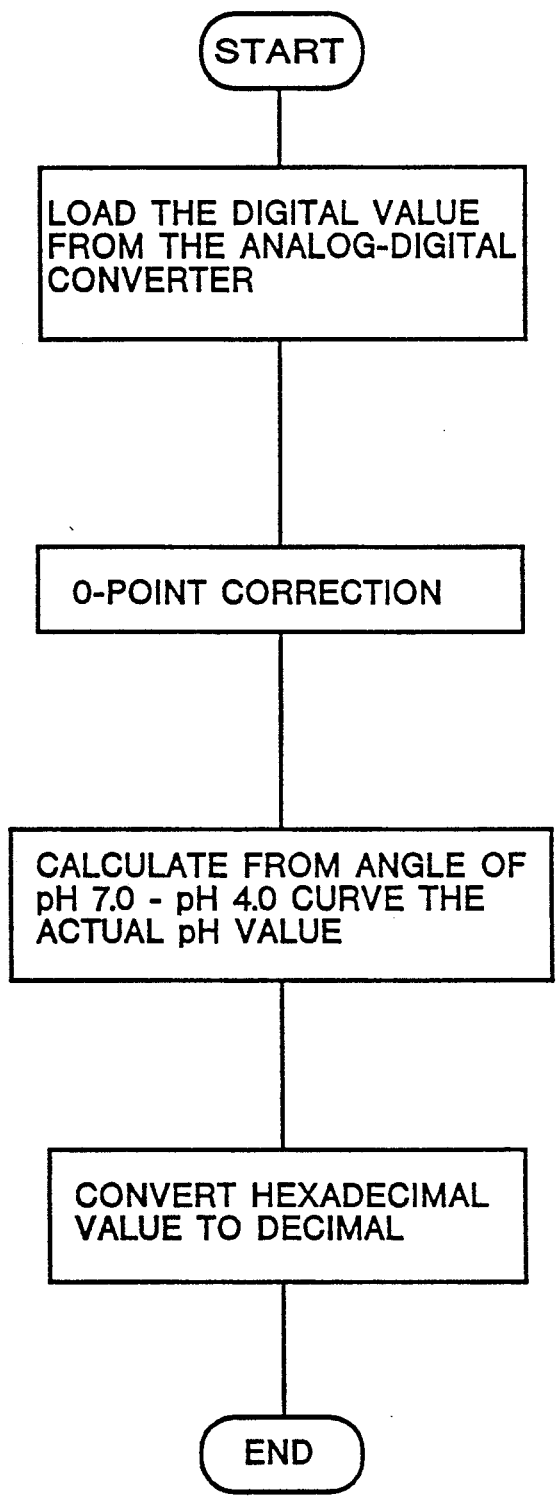
Figure 2E:
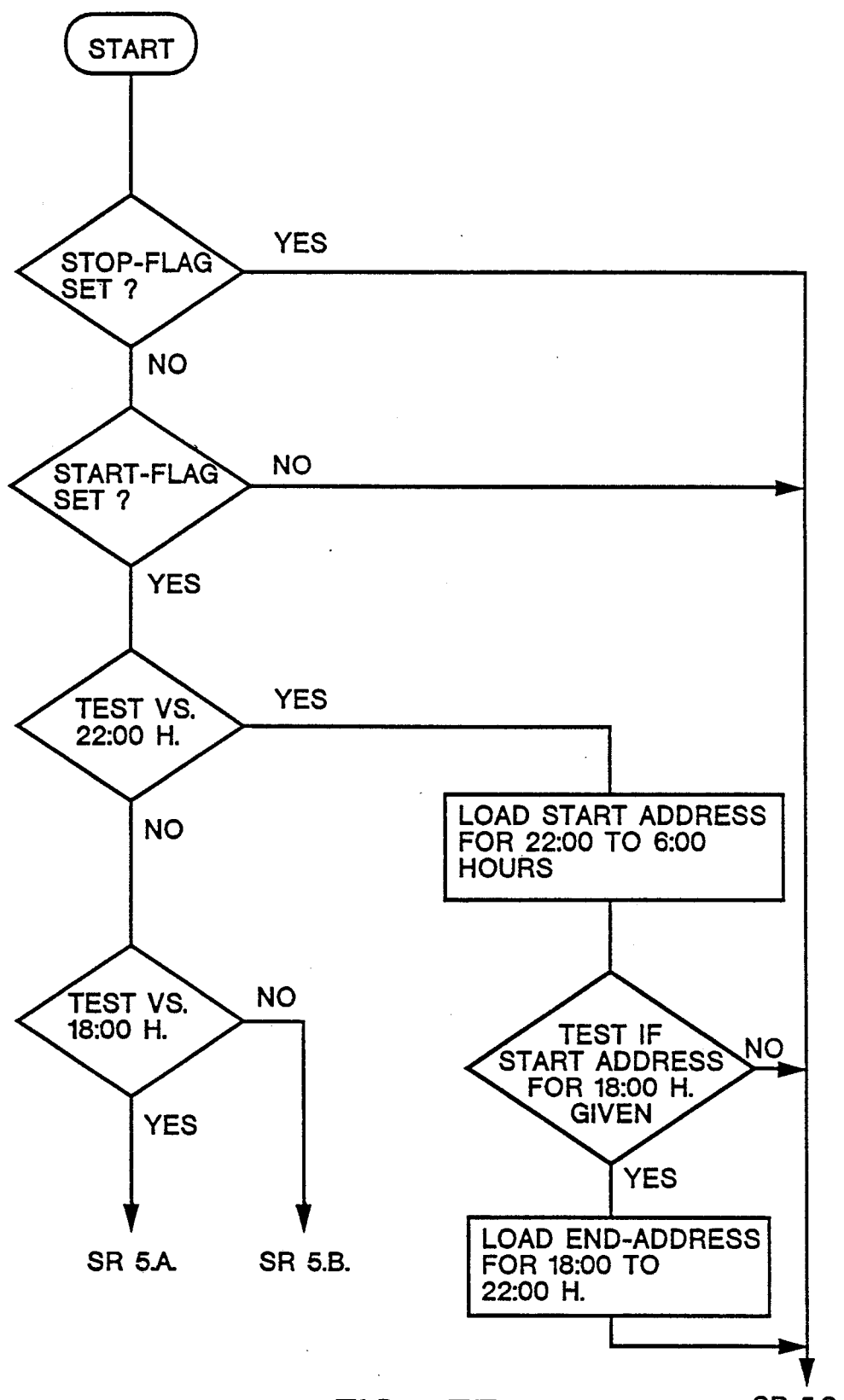
Figure 2F:
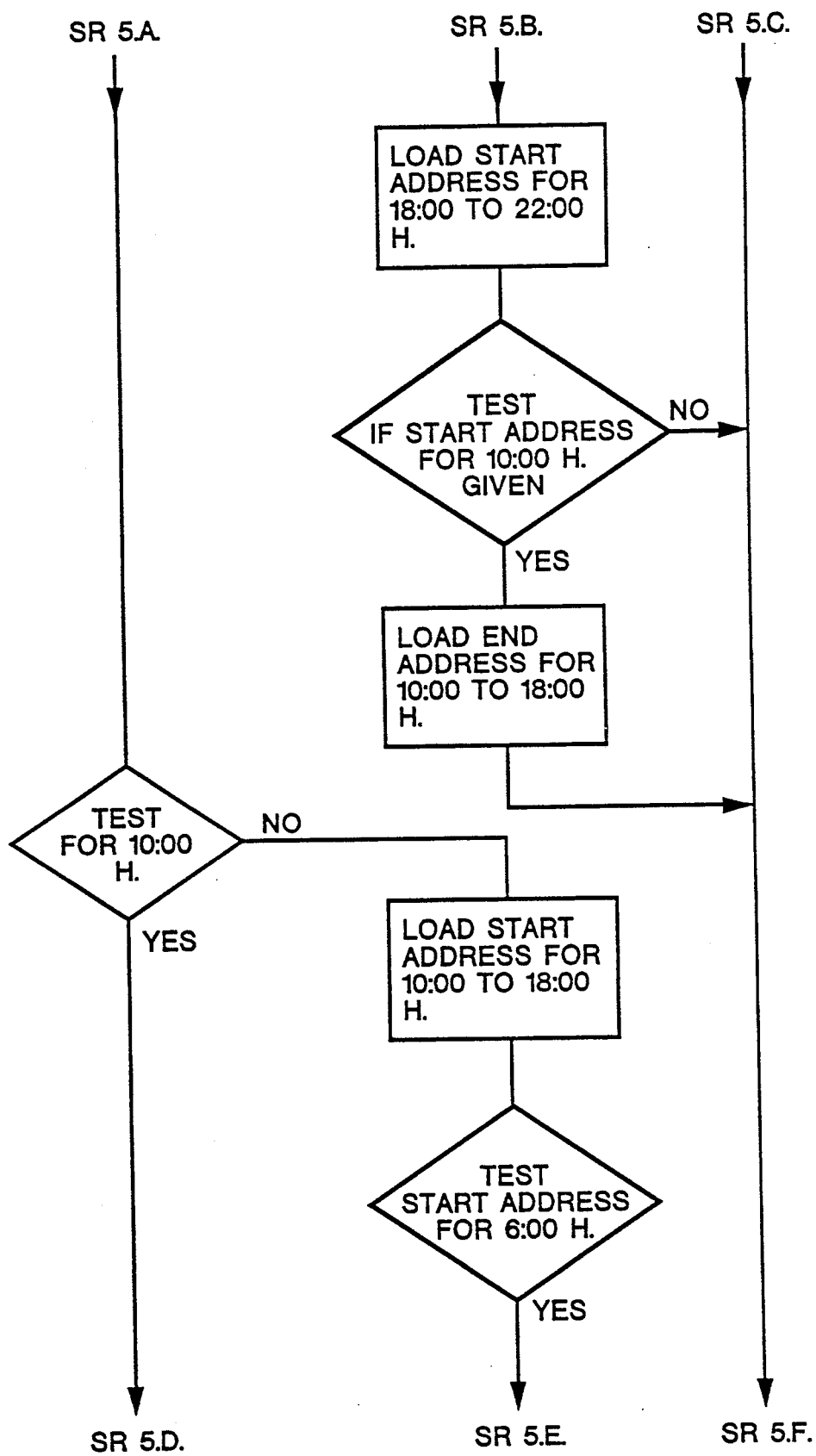
Figure 2G:
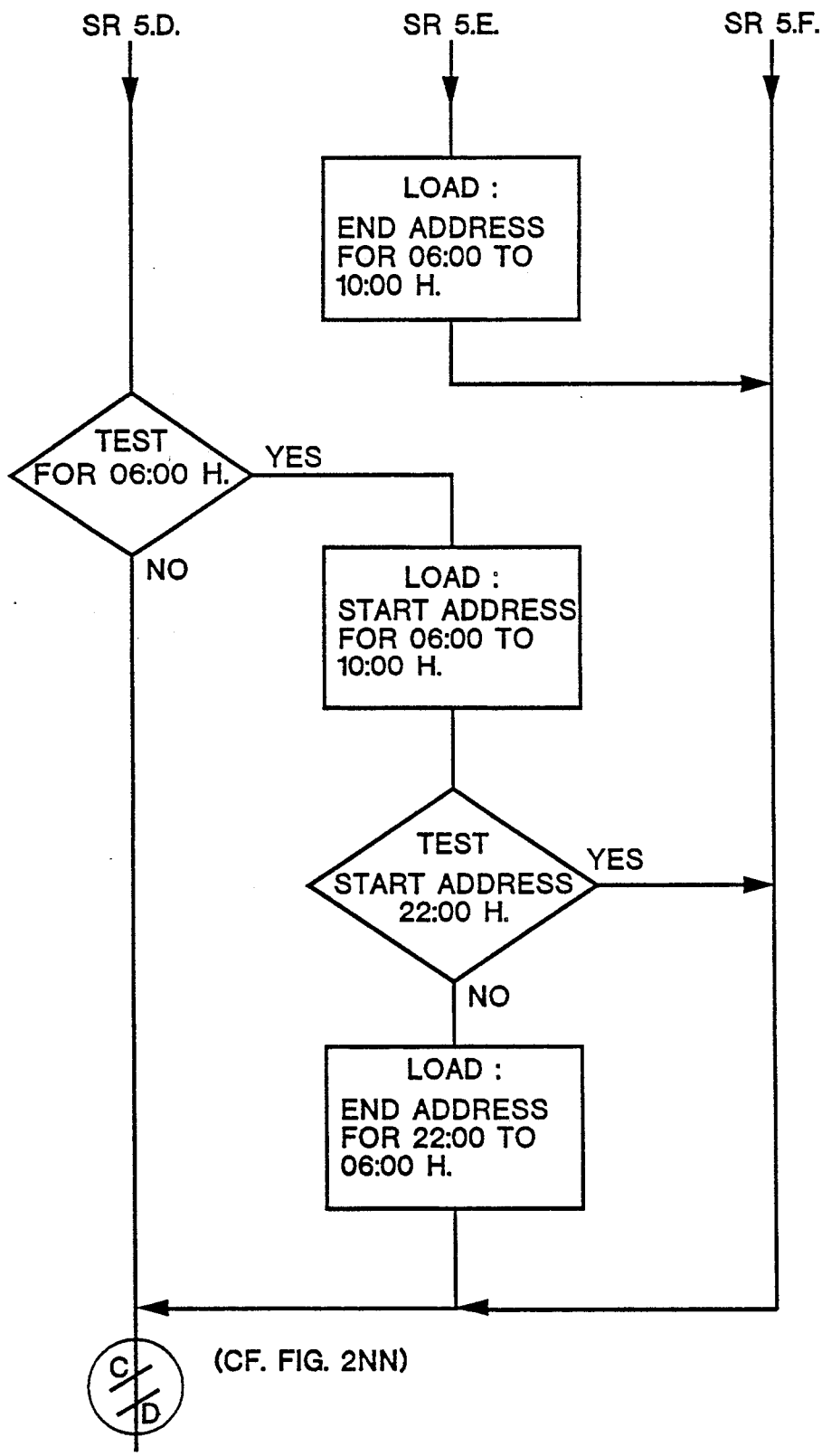
Figure 2H:
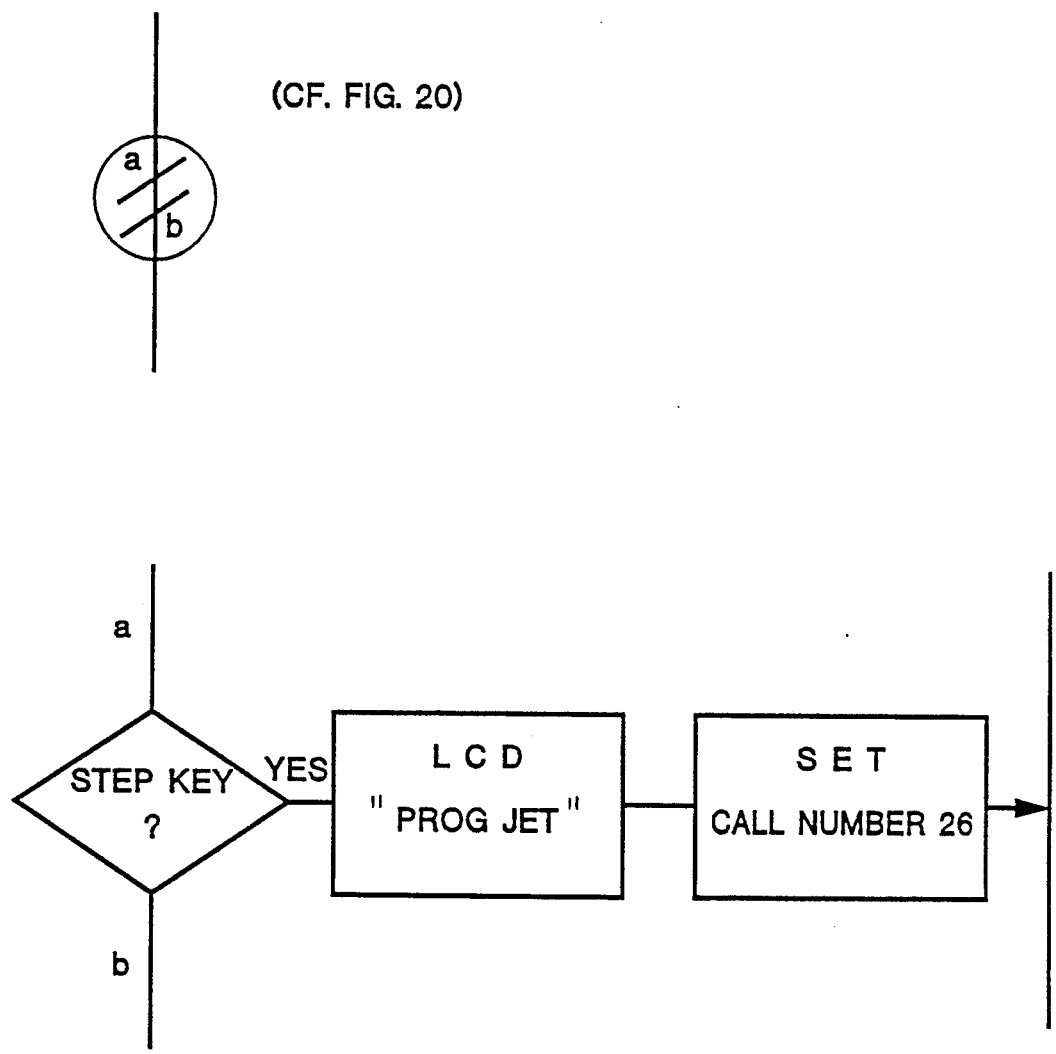
Figure 2:
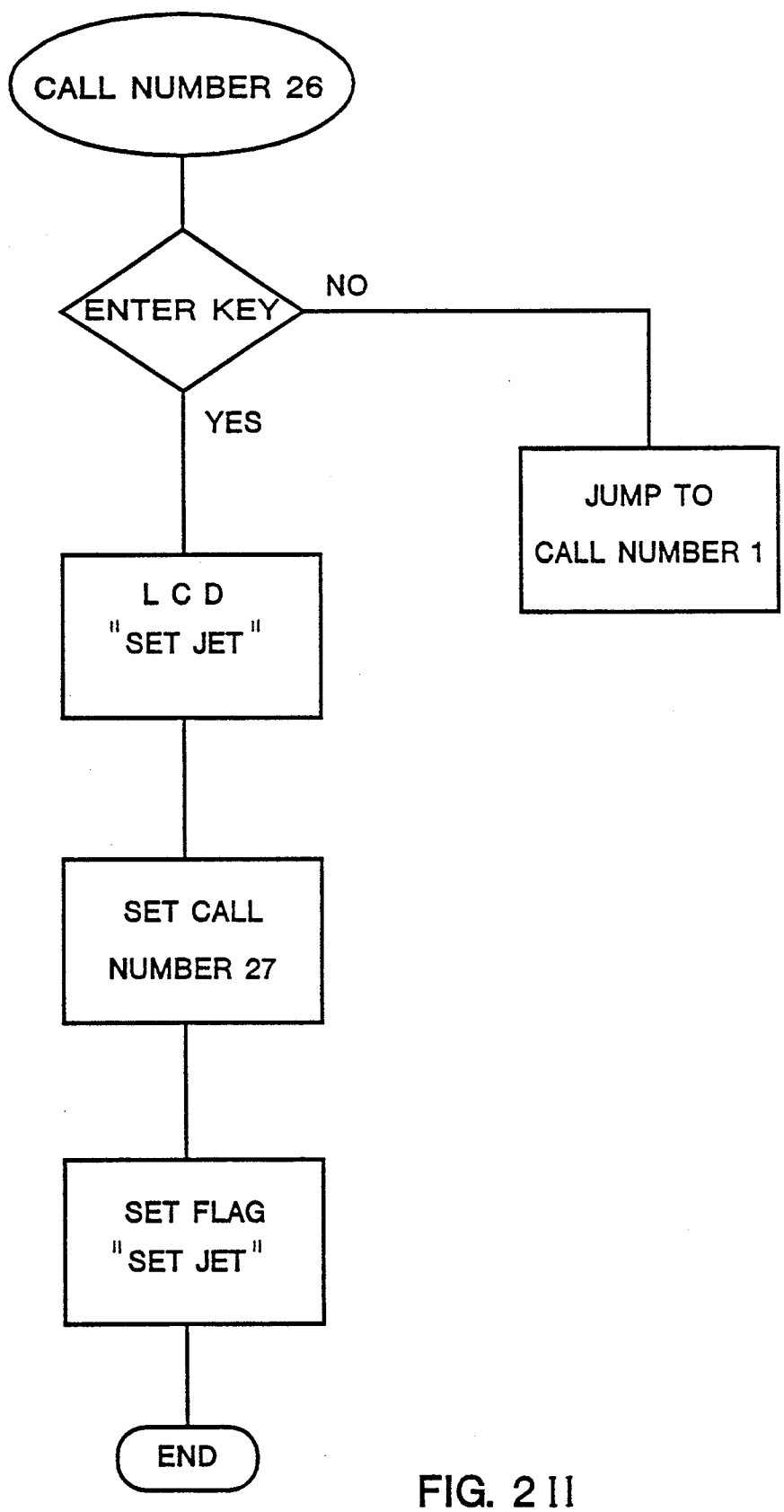
Figure 2J:
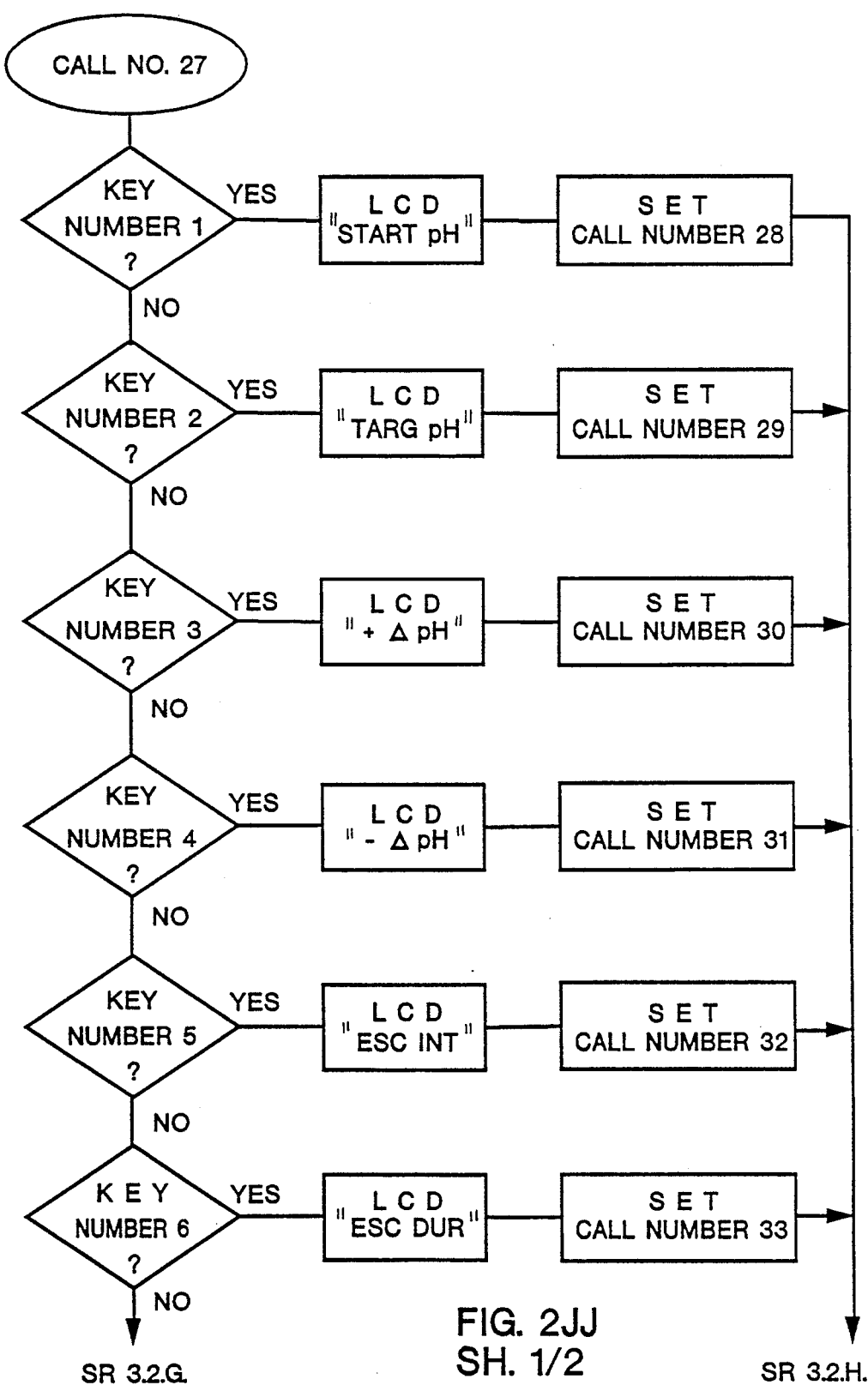
Figure 2U:
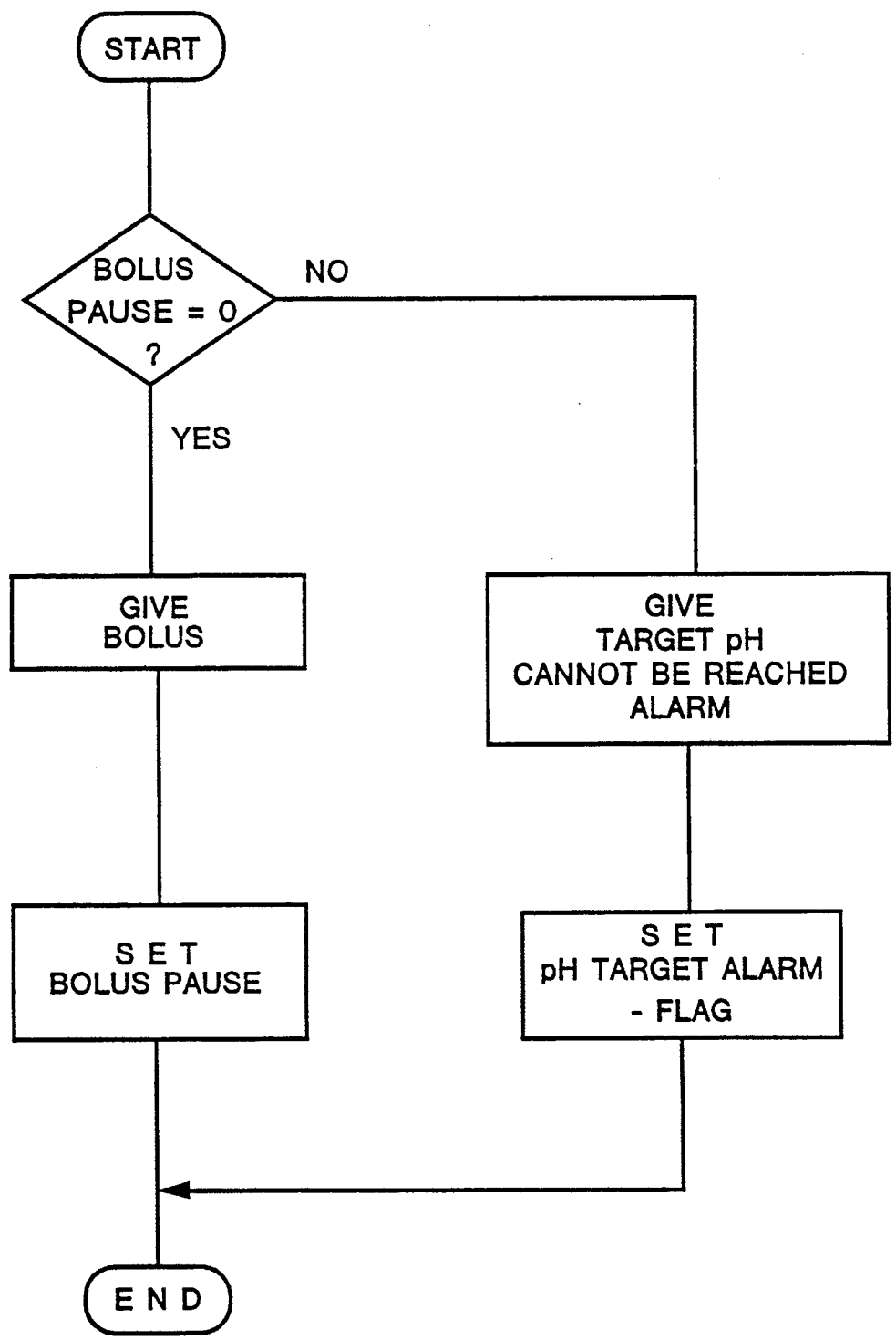
Figure 2J:
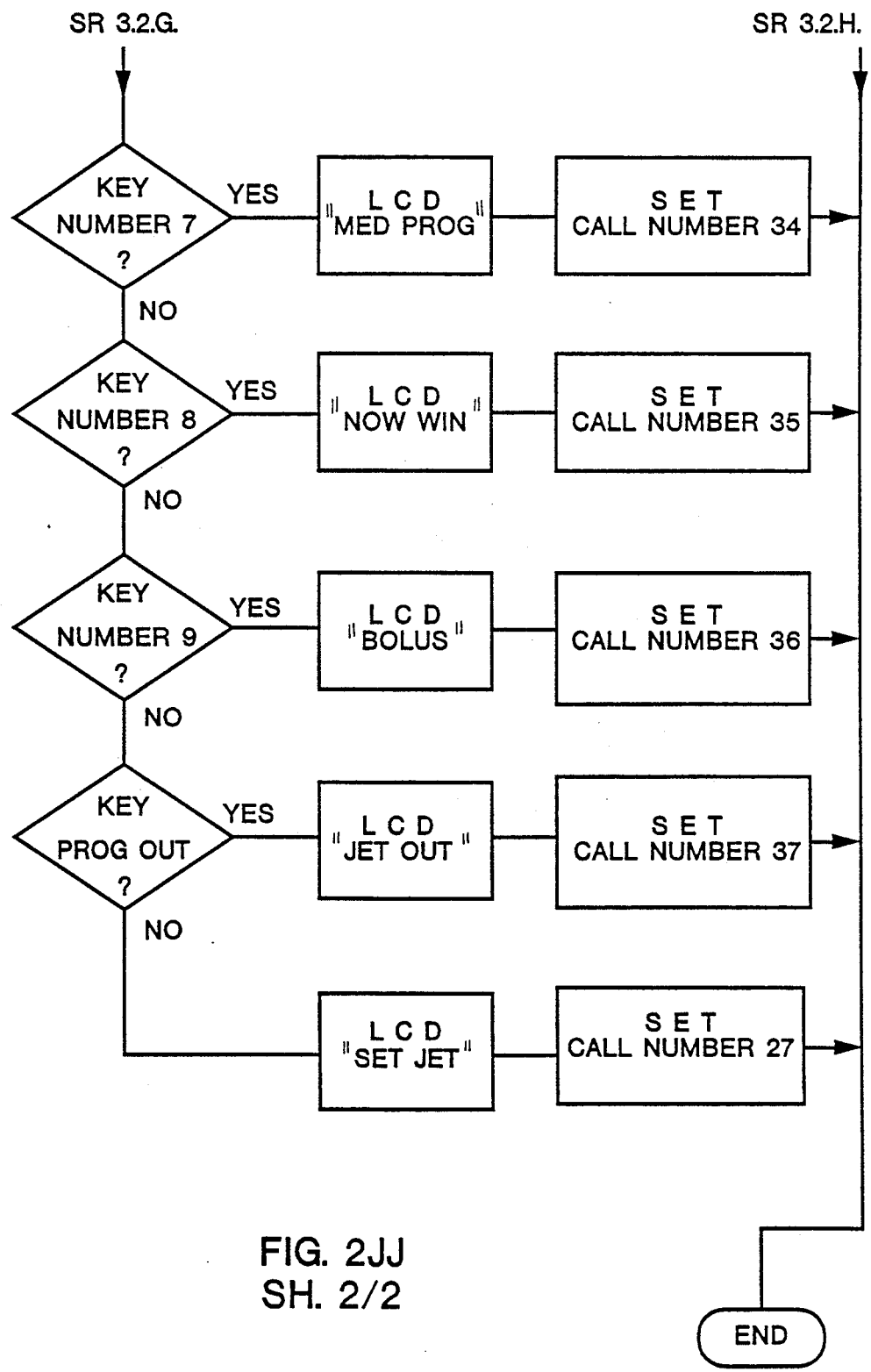
Figure 2K:
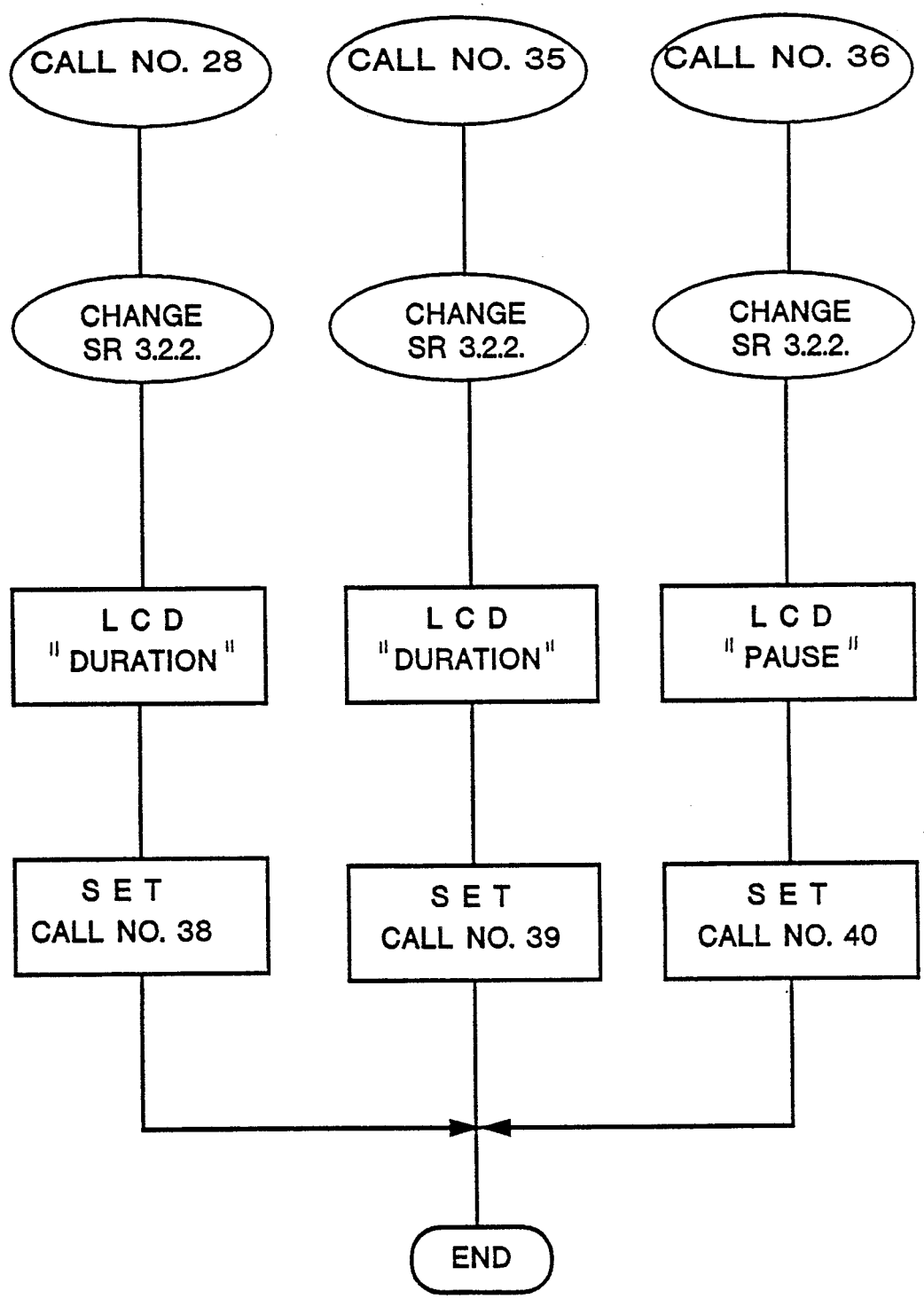
Figure 2L:
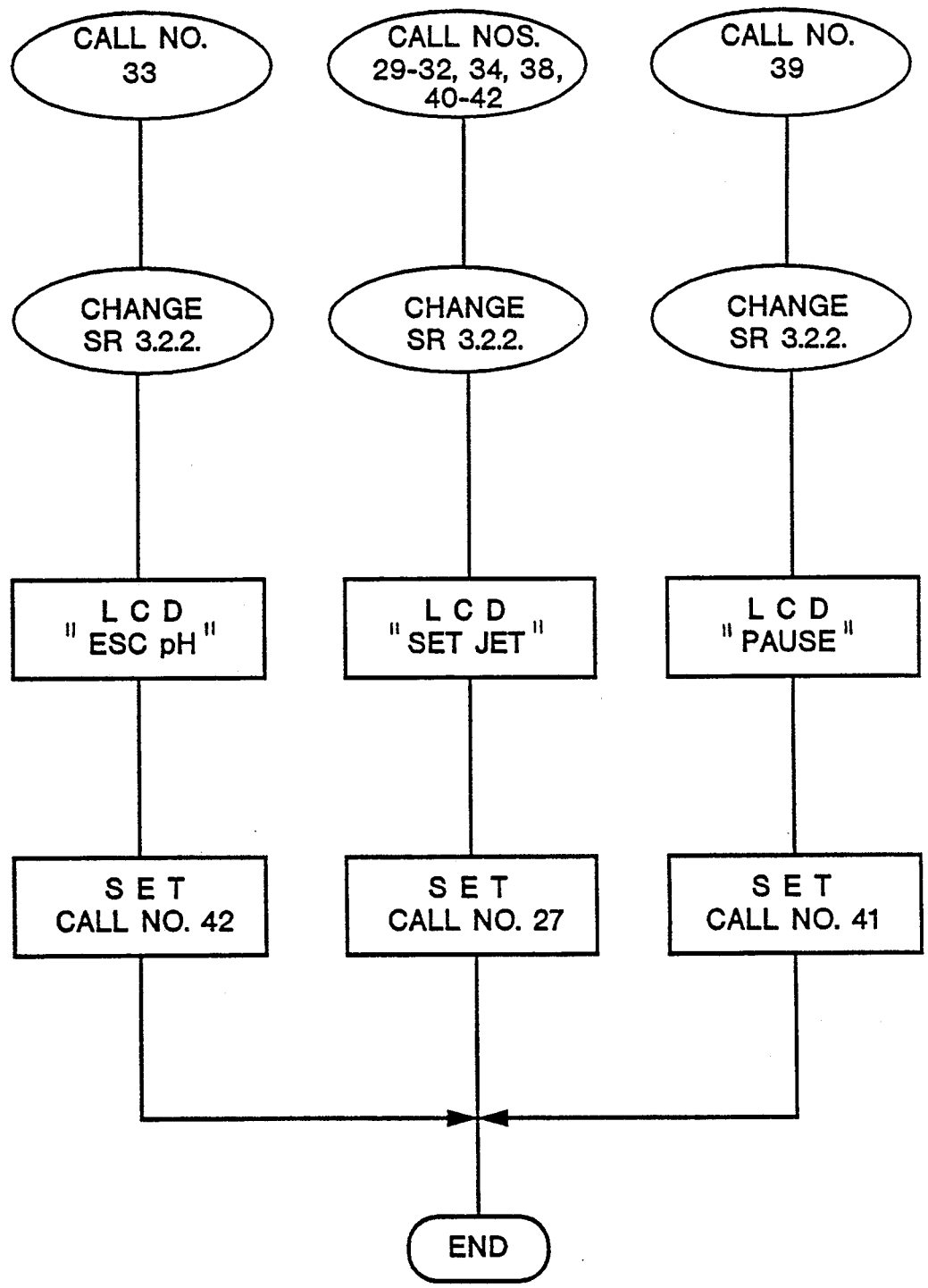
Figure 2M:
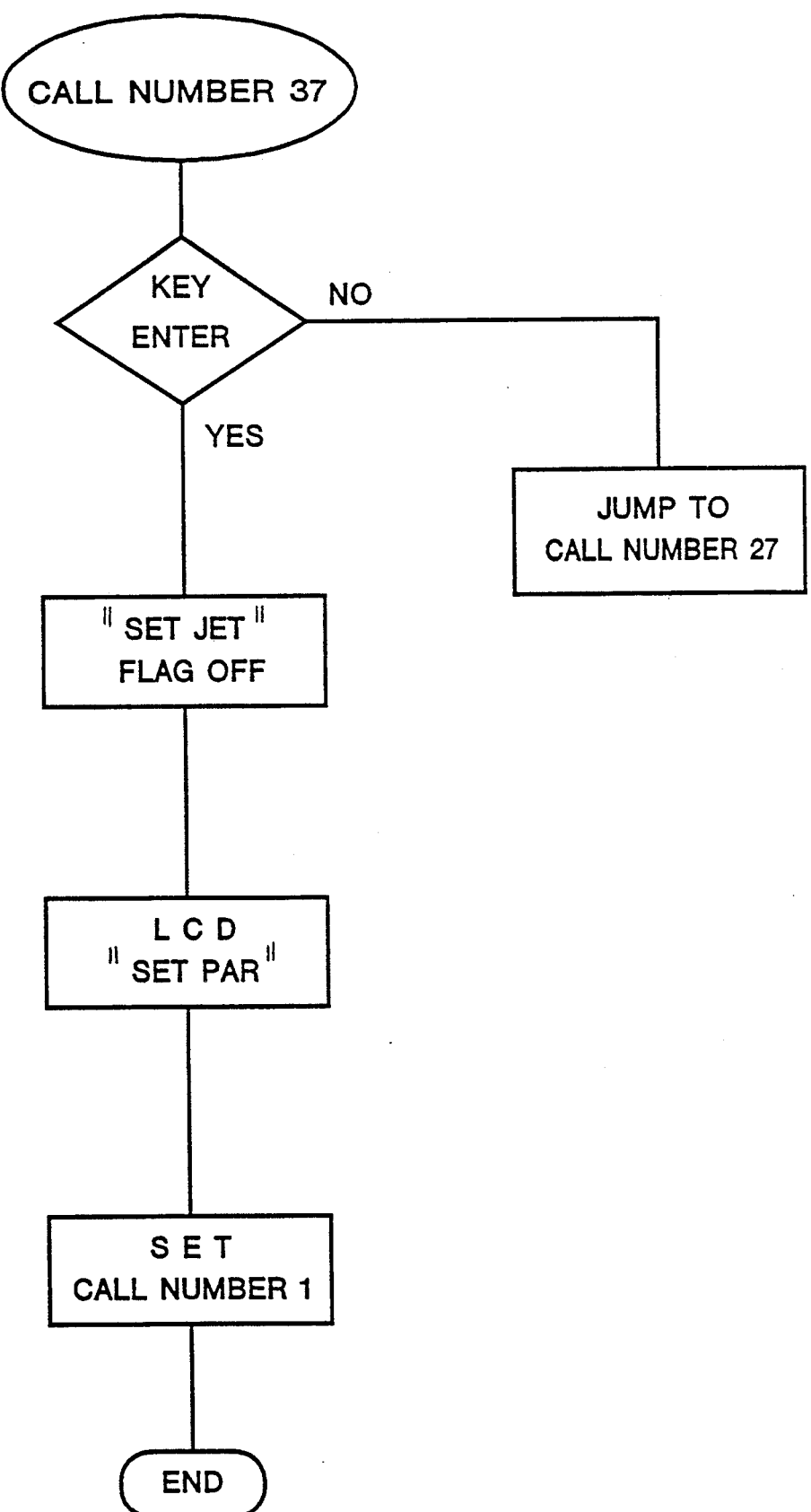
Figure 2N:
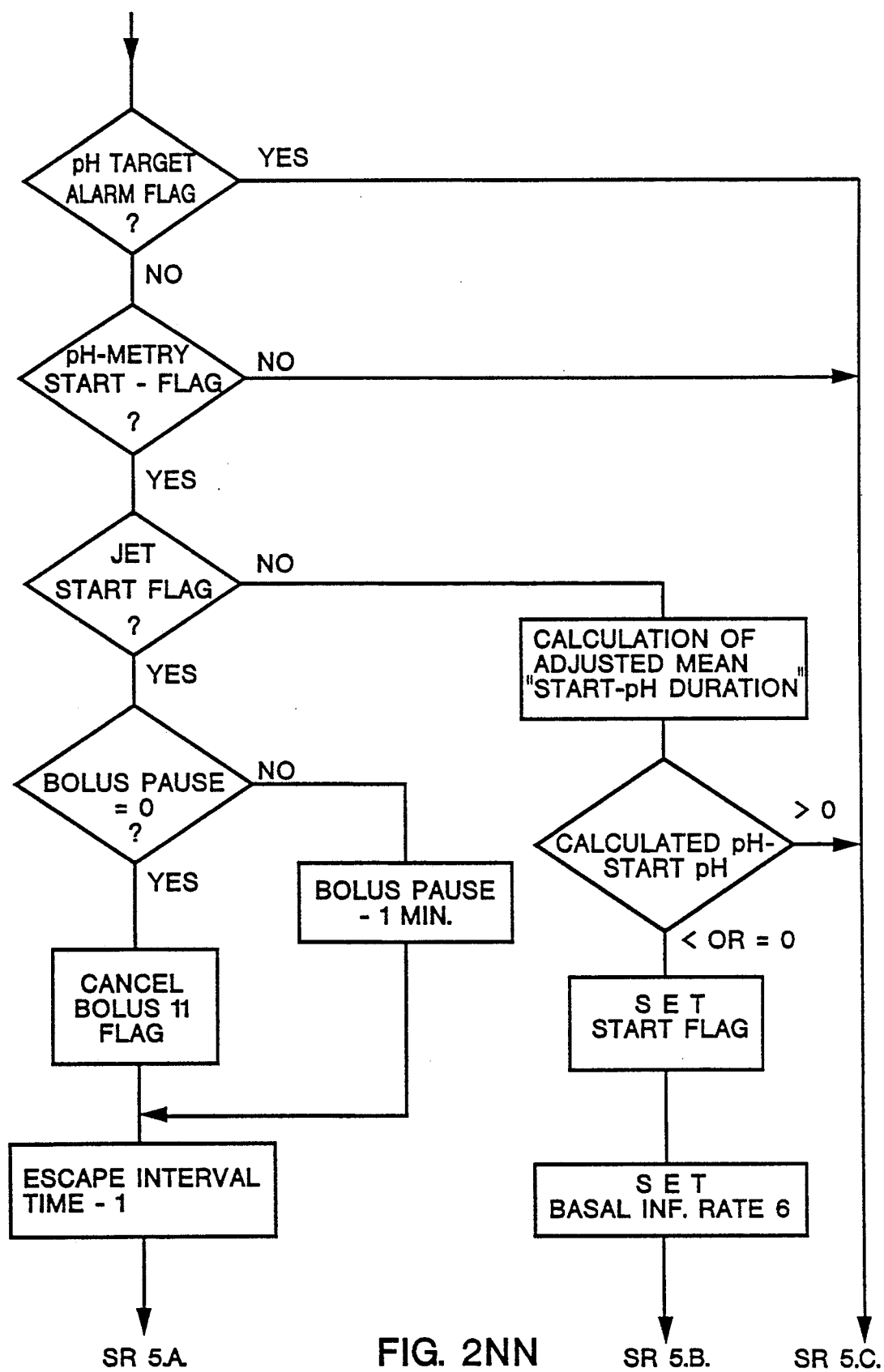
Figure 200:
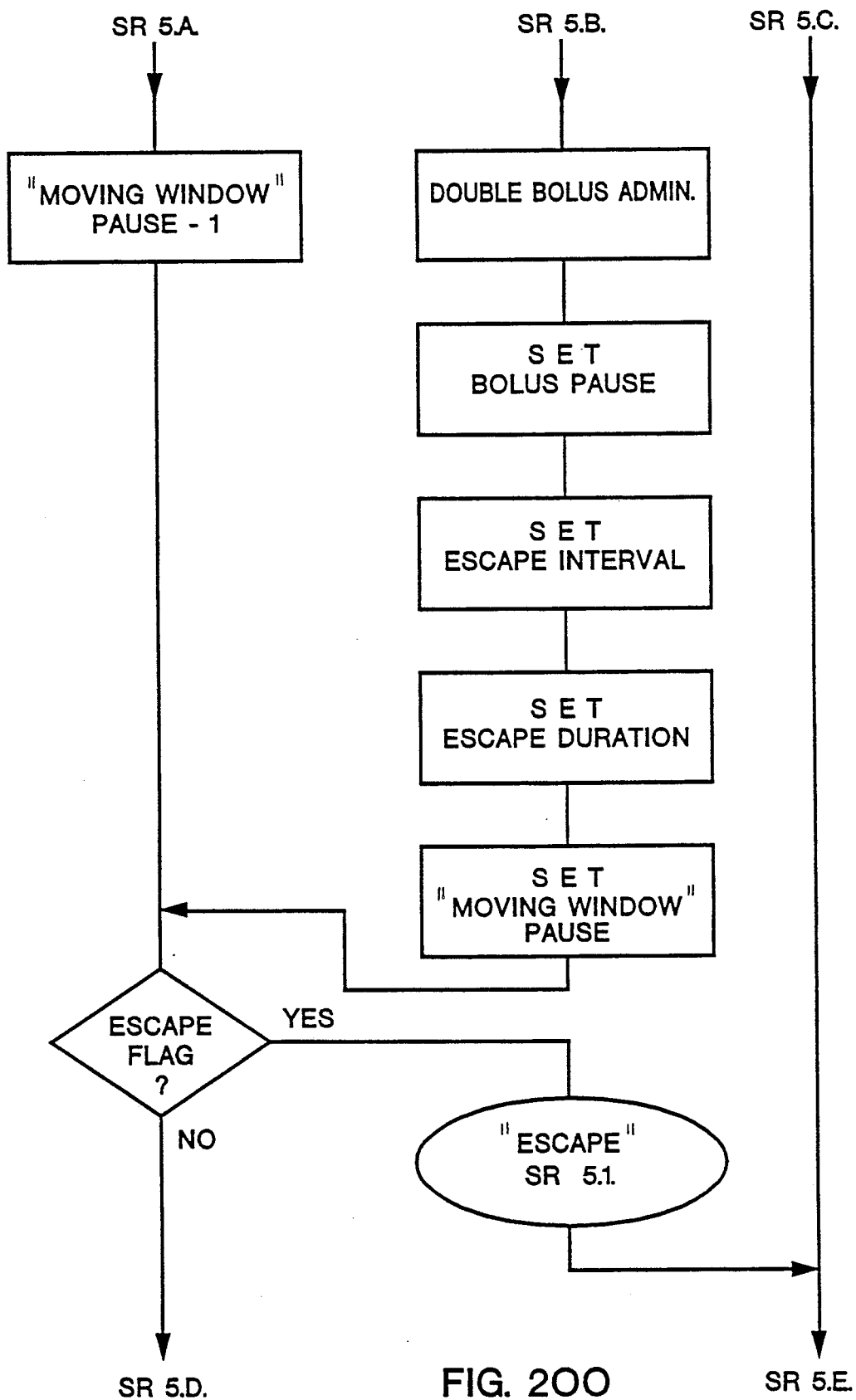
Figure 2P:
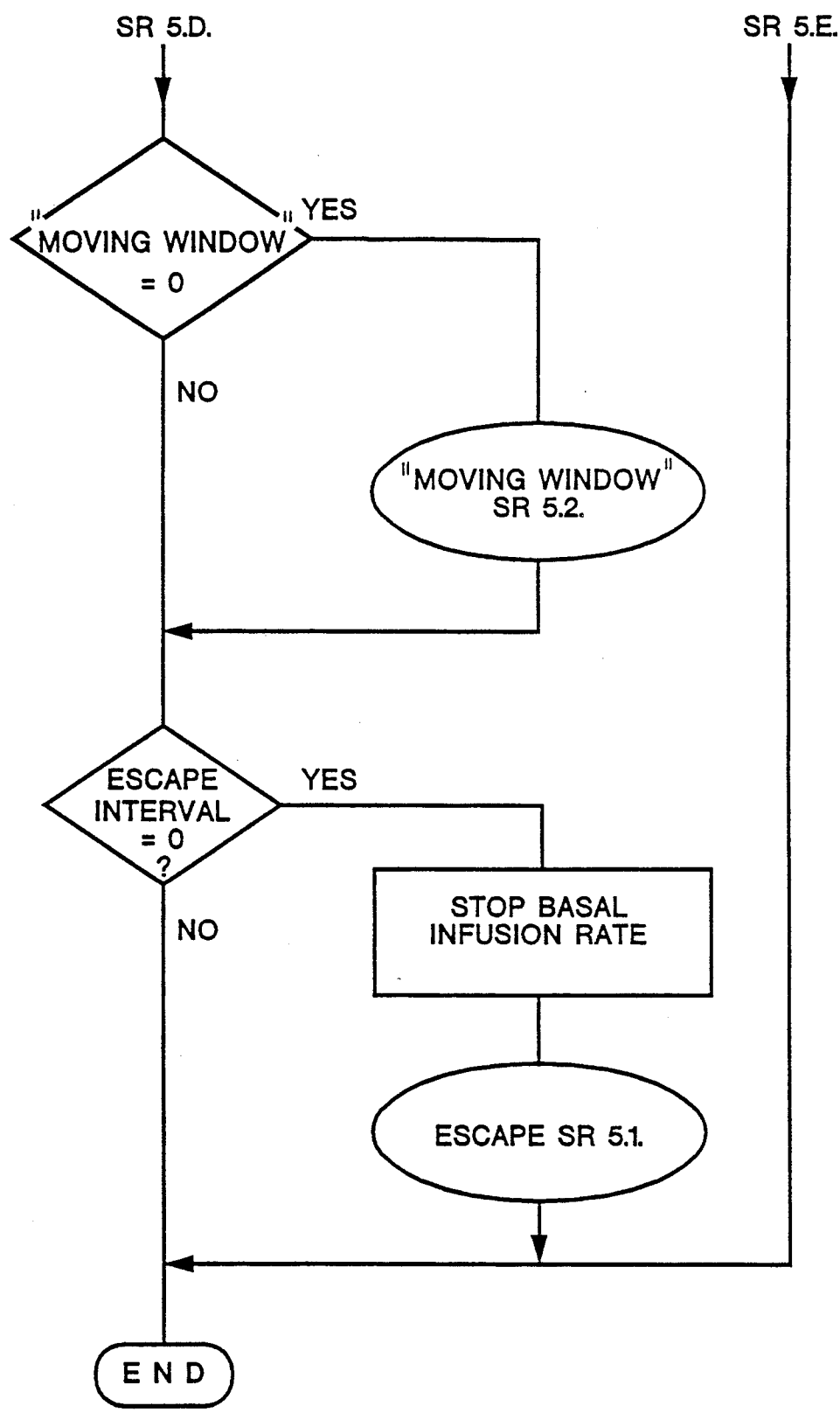
Figure 2Q:
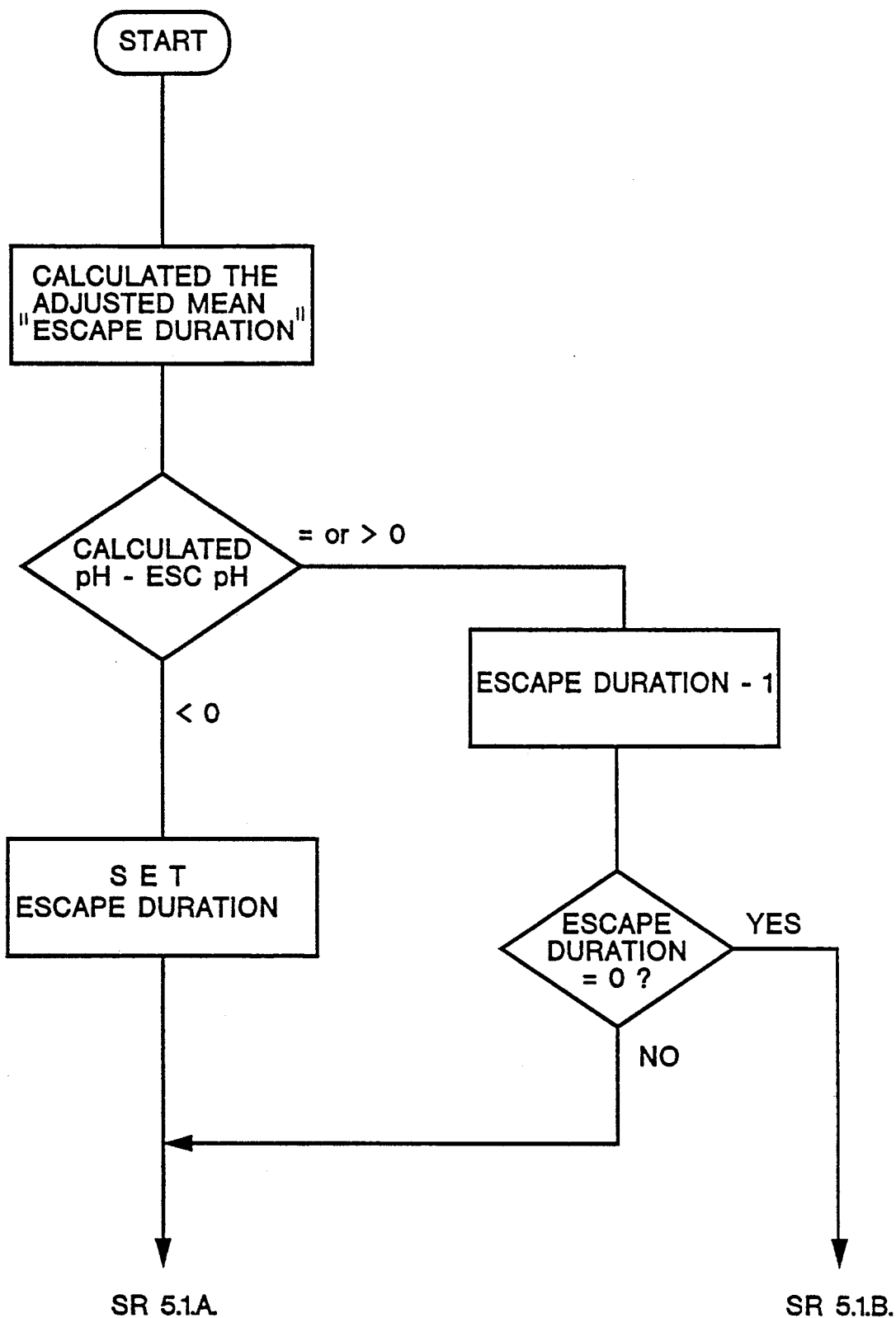
Figure 2R:
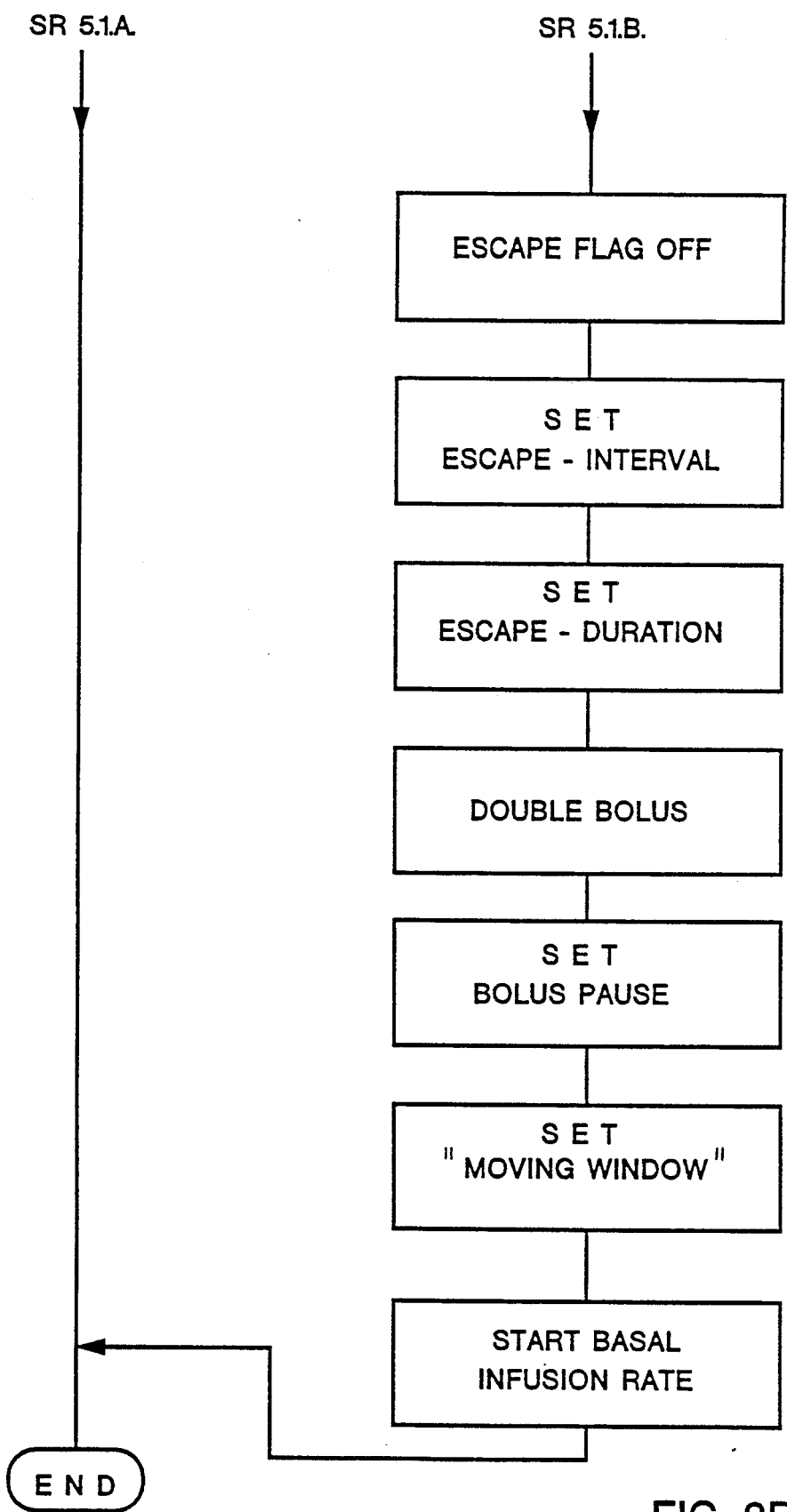
Figure 2S:
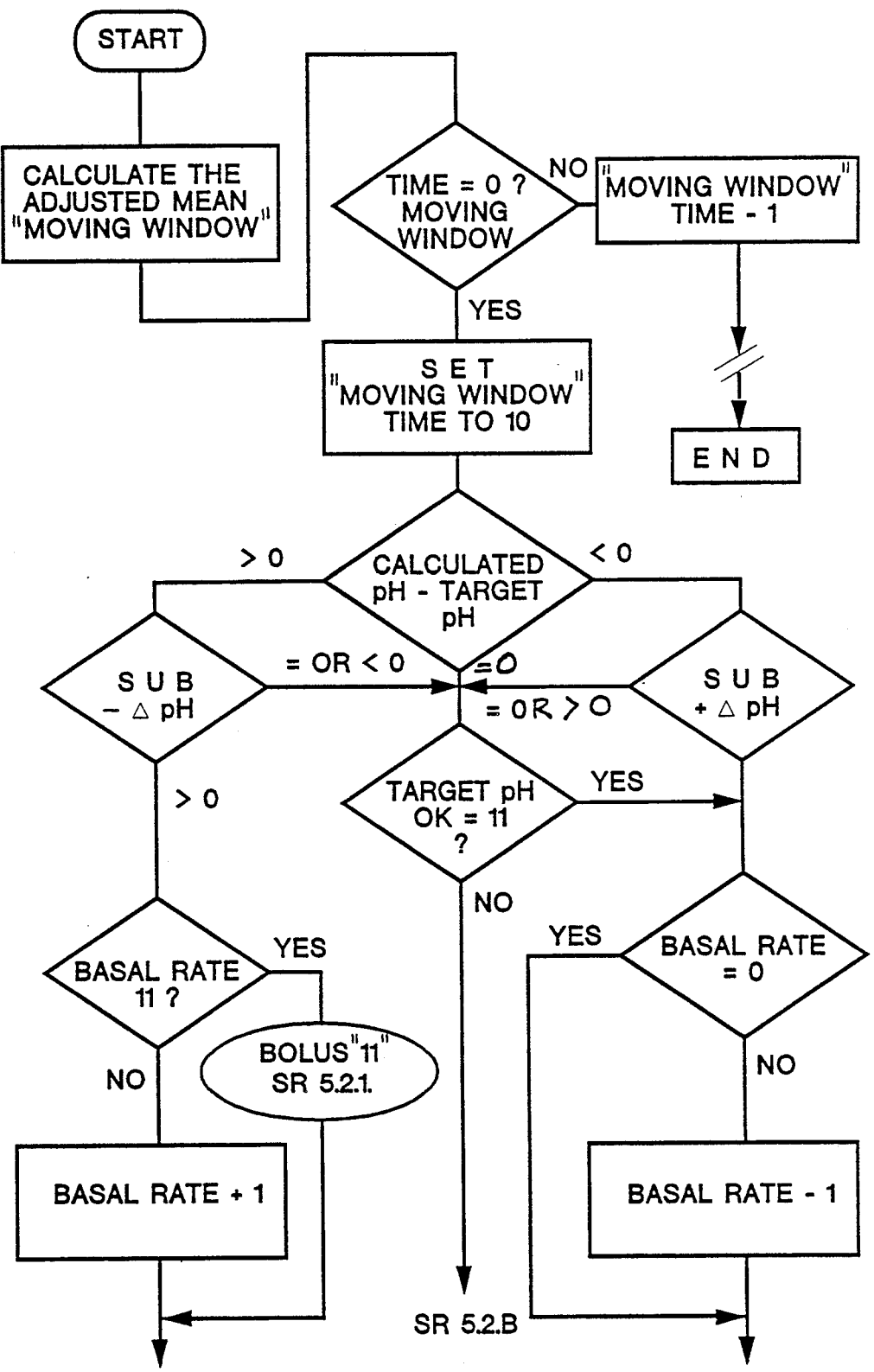
Figure 2T:
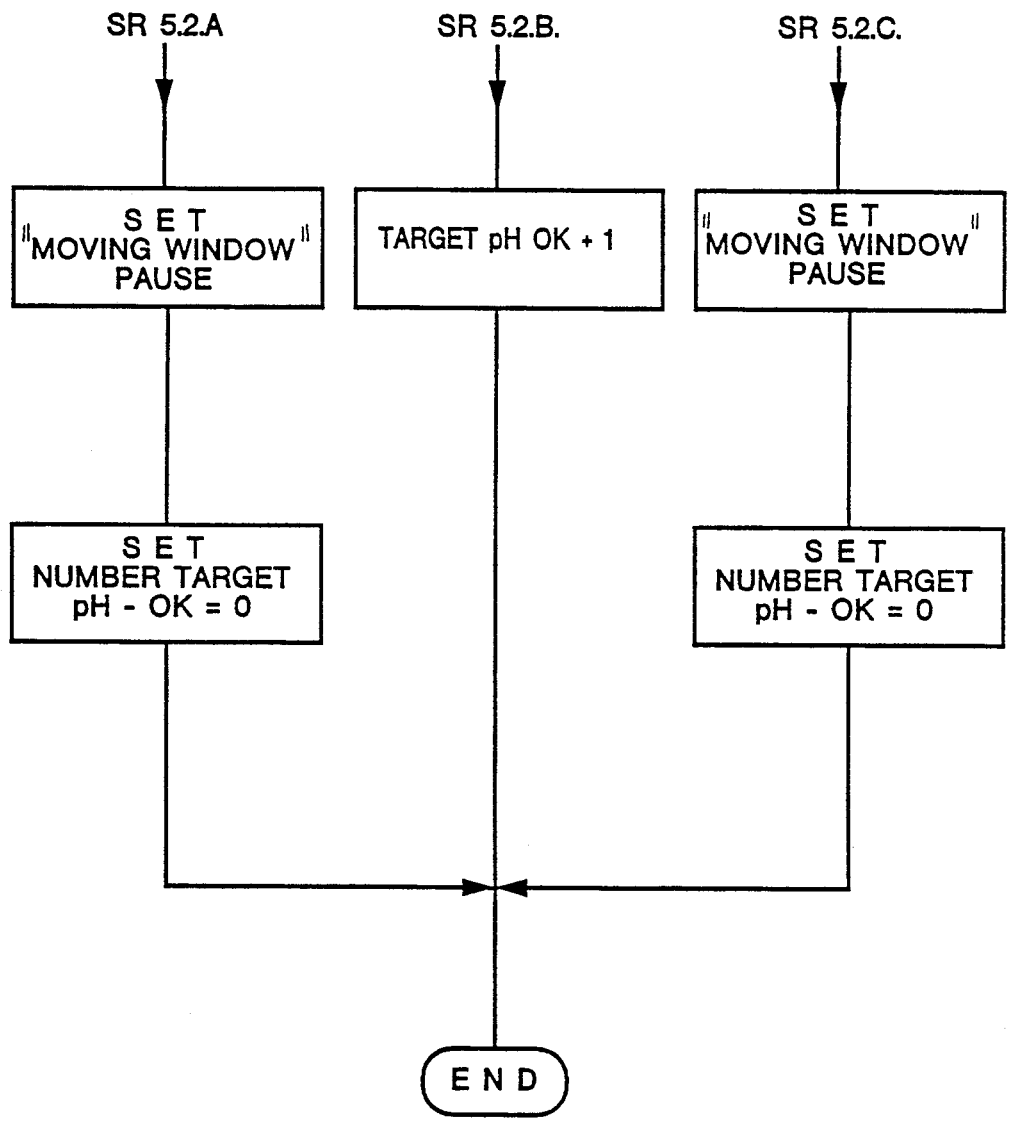

The biofeedback control apparatus shown in FIG. 1 has a sensor system which comprises one or more sensors, the drawing showing a pH-sensor 1, a blood pressure sensor 2 and a temperature sensor 3. It is obviously also possible to connect other sensors, e.g., those for measuring the pulse, respiratory rate, potential differences or biochemical parameters.

With the sensors 1, 2, 3 are associated amplifiers 4, 5, 6, which are connected to a multiplexer 7. The multiplexer is connected either through an A/D converter 8 or directly to a microcomputer 9 depending on whether a particular sensor is analog or digital. There are also one or more data memories 10, which store the values measured by the sensors and also contain reference and limit threshold values or ranges.

Microcomputer 9 has a keyboard 11 and is connected to an alphanumeric and/or graphic display 12 and an alphanumeric and/or graphic printer 13. The microprocessor 9 is also provided with a data transfer interface 14 for connection to an external computer, and controls an optical and/or acoustic alarm 15.

In addition to elements 1 to 15 shown in the upper part of the drawing, a therapy means is provided which has at least one pump controlled by a second microprocessor 16. In FIG. 1 two peristaltic pumps 17, 18 are shown, which deliver drugs for the intravenous or intra-arterial, as well as oral or intraluminal administration With each pump 17, 18 is associated a reservoir 19, 20 in the form of slide-in modules containing the drug to be administered in accordance with the diagnosis made by means of the sensors 1, 2, 3 and the microcomputer 9. To the reservoir 19, 20 is connected a tube 21, 22, which passes via pump 17, 18 to the patient. The slide-in unit of each reservoir 19, 20 is provided with an identification code, which is read by sensors 23, 24, e.g., an optoelectronic or magnetic type detector or the like. The slide-in units of the reservoir 19, 20 may also be provided level detectors 40, 41, which record the particular level of the drug in each of the reservoirs. In place of the level detector or in addition thereto, the level can also be determined by microprocessor 16, from the initial volume of the reservoir and the amount of drug administered through the pumps 17, 18.

Pumps 17, 18, sensors 23, 24 and detectors 40, 41 are connected both to the microcomputer 16 and to surveillance circuitry 25. The surveillance circuitry 25 receives information from the microcomputers 9, 16 to establish redundancy. For this purpose, the surveillance circuitry preferably has its own microprocessor 43 and receives vital parameters, such as the intra-arterial pressure through a second sensor system 44 similar to the primary system of elements 1-15 with a measurement evaluation unit and a comparison unit realized by the microprocessor. The values measured by the primary measuring and evaluating means 1 to 9 are compared with values obtained by the secondary sensor system 44. If differences occur, which indicate a probable failure of one of the two systems, an optical and acoustic alarm pulse is given through alarm 28. In this case, non-vital parameters, such as temperature or pH-value, are monitored by a backup program contained in the microprocessor 43 which takes over the main program. The therapy means also has suitable peripheral equipment, such as a display 26, keyboard 27 which are connected to microprocessor 16 and surveillance circuity 25.

Obviously microcomputers 9 and 16 can be combined to form a single unit, it then only being necessary to have one keyboard, one display and one alarm.

The apparatus according to the invention is connected to a commercial power supply but also has its own power supply 29 using dry-cell batteries or primary batteries. In the case of a failure of the commercial power supply, the supply 29 can maintain operation for a long time (6 to 8 hours).

The apparatus according to the invention functions as follows. The ideal values or ranges of preselected body functions of the patient measured by sensors 1, 2, 3 at preselected time intervals are stored in memory 10 or in another memory of microcomputer 9 and are optionally converted mathematically, e.g., for determining standard deviation values, median values or the like. The measured values are compared with predetermined reference values stored in memory 10 or with external reference values fed in by the doctor by means of keyboard 11 and are interpreted in accordance with a diagnosis program stored in microcomputer 9.

Microcomputers 9 and/or 16 store therapy objectives, side maximum drug doses, dosages over certain time intervals and the nature of the drug administration. As a function of the diagnosis determined with the aid of the measured values, the therapy means is activated, i.e., microcomputer 16 activates one or more pumps 17, 18 and either stimulating or inhibiting drugs can be administered. Prior to activation, the sensors 23, 24 read the identification codes which identify the particular drug in the slide-in container, so that erroneous infusion of incorrect drugs is not possible. Microcomputer 16 can activate pumps 17, 18 in such a way that the drugs are administered continuously, intermittently or in bolus-like manner, (i.e., in a single relatively large dosage). Alternatively to combine pulsatile or continuous administration with bolus administrations.

The biological body functions which are of interest are measured by means of sensors 1, 2, 3, simultaneously with the administration of the drugs so that the effects of the therapy are continuously monitored. Optionally the drug administration can be modified or ended or some other drug can be administered.

The apparatus may be used to follow a preselected therapy programmed in the computer for delivering precalculated medication doses. Alternatively, the computers may be programmed for investigating the body functions in response to a preselected daily doses or a preselected dose administered for shorter time periods. Displays 12, 26 make it possible to show all the collected data and provide data and therapy functions over the entire course of treatment. Correspondingly all the data can be printed out by means of printer 13.

Alarms 15, 28 supply optical and/or acoustic alarm signals if the functions of the individual components of the apparatus, the types and amounts of drugs in the reservoir, or the values or the therapy objectives do not coincide with the predetermined or desired values indicated by diagnosis.

Two examples for using the subject apparatus are given below. In the first example, a gastric pH control is carried out via a synergistic therapy by using pumps 17, 18, for administering drugs having similar effects. In the second example, a blood pressure control is demonstrated for using antagonistic therapy functions in which the pumps are used to obtain opposite effects.

1. Gastric-pH control

The pH-sensor 1 intraluminally measures the H+-ion activity. The measured data are stored and compared with the reference values stored in the microprocessor. For setting the therapy objective, e.g., raising the pH-value, microprocessor 12 activates the first pump for the administration with standard drugs, e.g., H2-antagonist or ATP-ase inhibitors, either as a primed infusion, i.e., a bolus, followed by a continuous infusion or an intermittent infusion. The standard doses administered by the pump are increased or decreased stepwise by comparing the therapy objective with the patient's response. After a preselected time period, the effectiveness of the therapy is determined using a preset criteria. The time adaptation and definition of the therapy success/failure is predeterminable. If the therapy objective fails despite maximum dosage, either an alarm is given or the second pump is activated with a combination preparation. The therapy steps for the second pump are carried out similarly to the steps for the first pump.

2. Blood pressure

Two or three independent pressure sensors intra-arterially measure blood pressure, which is compared with the target pressure over clearly defined time periods. The adaptation of the existing pressure to the target pressure takes place with readily controllable drugs, the drugs associated with the first pump increasing the pressure, while those associated with the second pump being able to reduce the pressure. The system can be provided with one or two additional, series-connected pumps, which are able to administer additional synergistic or antagonistic medicaments. The sensor functions are continuously monitored by the apparatus and the measured data of the two or three sensors are compared with one another. If divergences occur which are greater than a predetermined value, an alarm is given and the pumps are disabled.

We claim:

1. An apparatus for biofeedback control of body functions of a patient, which comprises:

first means for sensing and detecting biological body values relating to the patient;

a memory device for storing reference values;

means for providing intravenous, intra-arterial, oral or intraluminal administration of a preselected mediciment to the patient;

a reservoir coupled to the means for providing administration of a preselected mediciment, said reservoir arranged to contain a supply of the preselected mediciment;

means for controllably activating said means for providing administration of a preselected mediciment as a function of the biological body values detected by the first means and the reference values stored in the memory device;

second means for sensing and detecting the biological body values;

means for comparing the biological body values detected by each of the first and second means for sensing and detecting; and an output device coupled to the means for comparing and operating to output an alarm signal when said means for comparing indicates a predetermined divergence between the biological values detected by the first and second means for sensing and detecting.

2. The apparatus according to claim 1 wherein said means for providing administration of a preselected mediciment includes a pump coupled to said reservoir.

3. The apparatus according to claim 2 wherein said pump comprises a peristaltic pump.

4. The apparatus according to claim 2 wherein said pump operates in one of a continuous, intermittent and bolus-like manner.

5. The apparatus according to claim 1 wherein said means for providing administration of a presselected mediciment includes a plurality of pumps, each pump being coupled to an associated reservoir wherein a preselected mediciment received in one reservoir has one of a synergistic or antagonistic action relative to a preselected mediciment received in another reservoir.

6. The apparatus according to claim 1 wherein each of said first and second means for sensing and detecting includes at least one sensor selected from the group consisting of a pH-sensor, a pressure sensor, a temperature sensor and the like.

7. The apparatus according to claim 1 further comprising means for detecting a filling level of said reservoir.

8. An apparatus for biofeedback control of body functions of a patient, which comprises:
- means for sensing and detecting biological body values relating to the patient;
- a memory device for storing reference values;
- means for providing intravenous, intra-arterial, oral or intraluminal administration of a preselected mediciment to the patient;
- a reservoir coupled to the means for providing administration of a preselected mediciment, said reservoir arranged to contain a supply of the preselected mediciment;
- means for controllably activating said means for providing administration of a preselected mediciment as a function of the biological body values detected by the means for sensing and detecting and the reference values stored in the memory device;
- said reservoir including an identification marking to identify a mediciment contained in said reservoir; and
- said means of controllably activating said means for providing administration including a sensor for automatically scanning said identification marking to identify the mediciment contained in said reservoir and operating to verify that the mediciment contained in said reservoir comprises the preselected mediciment.

* * * * *